US011887709B2

(12) United States Patent
Soe et al.

(10) Patent No.: US 11,887,709 B2
(45) Date of Patent: Jan. 30, 2024

(54) SYSTEMS AND METHODS FOR PREDICTING RECOVERY OF A PATIENT

(71) Applicant: NEC Corporation, Tokyo (JP)

(72) Inventors: Ni Ni Soe, Hyflux Innovation Centre (SG); Charles Choy, Hyflux Innovation Centre (SG)

(73) Assignee: NEC CORPORATION, Tokyo (JP)

(*) Notice: Subject to any disclaimer, the term of this patent is extended or adjusted under 35 U.S.C. 154(b) by 450 days.

(21) Appl. No.: 17/271,921

(22) PCT Filed: Aug. 23, 2019

(86) PCT No.: PCT/JP2019/033107
§ 371 (c)(1),
(2) Date: Feb. 26, 2021

(87) PCT Pub. No.: WO2020/050065
PCT Pub. Date: Mar. 12, 2020

(65) Prior Publication Data
US 2021/0319867 A1 Oct. 14, 2021

(30) Foreign Application Priority Data
Sep. 3, 2018 (SG) .......................... 10201807529V

(51) Int. Cl.
*G16H 10/60* (2018.01)
*G16H 15/00* (2018.01)
(Continued)

(52) U.S. Cl.
CPC ............. *G16H 10/60* (2018.01); *G16H 15/00* (2018.01); *G16H 40/63* (2018.01); *G16H 50/20* (2018.01)

(58) Field of Classification Search
CPC ........ G16H 10/60; G16H 15/00; G16H 40/63; G16H 50/20
(Continued)

(56) References Cited

U.S. PATENT DOCUMENTS

2014/0018299 A1* 1/2014 Mondello .......... G01N 33/6896
514/17.7
2015/0018664 A1* 1/2015 Pereira .................... G16H 50/20
600/410
2018/0127828 A1* 5/2018 Belli ....................... A61P 25/20

OTHER PUBLICATIONS

Tokunaga, Makoto et al., Increasing the prediction accuracy of FIM gain by adding RIM improvement for one month from admission to the explanatory variables in multiple regression analyses, Japanese Journal of Comprehensive Rehabilitation Science, vol. 8, pp. 1-5, Mar. 24, 2017 (Year: 2017).*

(Continued)

*Primary Examiner* — Joy Chng
(74) *Attorney, Agent, or Firm* — Sughrue Mion, PLLC

(57) ABSTRACT

Systems and methods predict functional and cognitive recovery of a person after the person has experienced a brain injury such as traumatic brain injury, cerebrovascular disease, and stroke. A computer system includes a database that stores multimodal data of the person recovering from a brain injury and a computer that analyzes the multimodal data over multiple intervals that span several months of time. The computer executes longitudinal heterogeneous trajectory analysis on the multimodal data and executes separation of heterogeneous groups that include good recovery potential of the brain injury, moderate recovery potential of the brain injury, and poor recovery potential of the brain injury. Based on the longitudinal heterogeneous trajectory analysis and the separation of the heterogeneous groups, the computer predicts functional recovery of the person from the brain injury.

20 Claims, 29 Drawing Sheets

(51) Int. Cl.
*G16H 50/20* (2018.01)
*G16H 40/63* (2018.01)

(58) Field of Classification Search
USPC .......................................................... 705/2–3
See application file for complete search history.

(56) References Cited

OTHER PUBLICATIONS

Kobayashi, Shuji, Prognosis prediction of stroke patients, Journal of the Japanese Physical Therapy Association, vol. 17, No. 1, pp. 6-8, Mar. 12, 2010 (Year: 2010).*
International Search Report for PCT Application No. PCT/JP2019/033107, dated Nov. 19, 2019.
Written opinion for PCT Application No. PCT/JP2019/033107, dated Nov. 19, 2019.
Tokunaga, Makoto et al., Increasing the prediction accuracy of FIM gain by adding FIM improvement for one month from admission to the explanatory variables in multiple regression analyses, Japanese Journal of Comprehensive Rehabilitation Science, vol. 8, pp. 1-5, Mar. 24, 2017.
Kobayashi, Shuji, Prognosis prediction of stroke patients, Journal of the Japanese Physical Therapy Association, vol. 17, No. 1, pp. 6-8, Mar. 12, 2010.

* cited by examiner

| Static Data Fields | Dynamic Data Fields |
|---|---|
| On Admission | Time points |
| Admission Date<br>Age<br>Gender<br>Height<br>Weight<br>BMI<br>Ethnicity<br>Education<br>Marital status<br>Social support<br>Employment status<br>Alcoholism consumption<br>Smoking behaviour<br>Blood pressure<br>Some comorbidity, such as hypertension, heart, kidney disease<br>Blood supply<br><br>Infratentorial ICH<br>Impairments<br>Side affected<br>Limbs affected part<br>MRI result<br>Complications<br>GCS<br>Modified Rankin Scale<br>NIHSS score<br><br>On Discharge<br><br>Discharge date<br>Premorbid ADL<br>Premorbid IADL<br>Discharge destination<br>Discharge ADL<br>Discharge IADL<br>Discharge social issues<br>Discharge Gait<br>Discharge level of assistance<br>Length of stay | Fugl Meyer Assessment of Motor Recovery<br>Berg Balance Scale (BBS)<br>Lawton IADL<br>Six-Minute Walk Test (6MWT)<br>Ten-Meter Walk Test<br>Trunk Impairment Scale<br>Mini-Mental State Examination (MMSE)<br>Mood_Depression<br>Mood_Anxiety<br>Mood_Stress<br>Patient Health Questionnaire-4 for feeling<br>Social Activity<br>Physiological assessment using EMG and motion sensor<br>Functional Independence Measure (FIM) |

Fig. 3

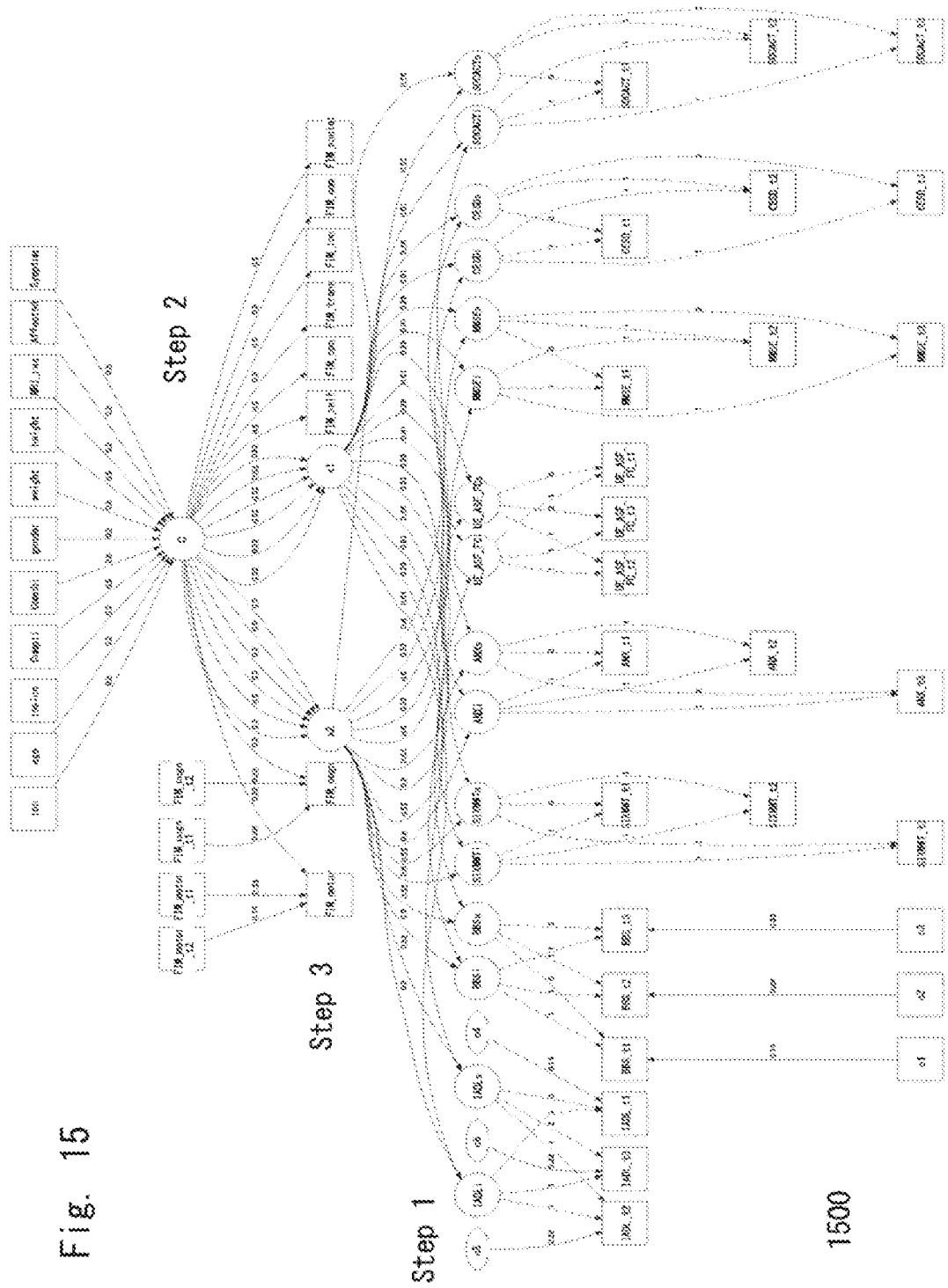

ized hospital resources.
SYSTEMS AND METHODS FOR PREDICTING RECOVERY OF A PATIENT This application is a National Stage Entry of PCT/JP2019/033107 filed on Aug. 23, 2019, which claims priority from Singapore Patent Application 10201807529V filed on Sep. 3, 2018, the contents of all of which are incorporated herein by reference, in their entirety.

TECHNICAL FIELD

The present invention generally relates to systems and methods that predict recovery of a patient after a brain injury.

BACKGROUND ART

Brain injuries, such as stroke and traumatic brain injury, are a leading cause of death and disability in the world. Predicting functional and cognitive recovery from such injuries are important measurements in rehabilitation planning and hospital resource utilization. Predicting potential recovery assists professionals in developing effective rehabilitation plans and in efficiently utilizing hospital resources. Besides, it will encourage therapists' confidence in engaging their intervention for patients, especially in junior therapists. Sometime, decisions about the rehabilitation potential may have far reaching consequences for individual patient. Such predictions can also motivate therapists themselves as well as patients to actively participate in rehabilitation training to meet well-defined goals.

One technical problem in this field is to develop computer systems and methods that can accurately make such recovery predictions. Such predictions are particularly challenging since patients' recovery patterns from brain injuries are unique and vary from patient to patient.

Example embodiments in accordance with the present invention solve these problems by providing systems and methods that more accurately predict patients' recovery after brain injury.

SUMMARY OF INVENTION

Technical Problem

Example embodiments of the present invention include a computer system and methods executed by the computer system that predict functional and cognitive recovery of a person after the person has experienced a brain injury. The computer system includes a database that stores multimodal data of the person recovering from a brain injury and a computer that analyzes the multimodal data over multiple intervals that span several months of time. The computer executes longitudinal heterogeneous trajectory analysis on the multimodal data and executes separation of heterogeneous groups that include good recovery potential of the brain injury in which their functional recovery are progressing quickly and may have a full functional abilities within 6 months, moderate recovery potential of the brain injury, in which their functional recovery are progressing slowly and may have a moderate functional abilities within 6 months, and poor recovery potential of the brain injury, in which their functional recovery are not much progressing and may have a limited functional abilities within 6 months. Based on the longitudinal heterogeneous trajectory analysis and the separation of the heterogeneous groups, the computer predicts functional recovery of the person from the brain injury.

Solution to Problem

Executing the longitudinal heterogeneous trajectory analysis on the multimodal data includes: selecting longitudinal time point data; fitting a model to the longitudinal time point data using one or more of linear modelling, quadratic modelling, and nonlinear modelling; and executing Bayesian information criterion (BIC) to choose a best fit model.

The separation of heterogeneous groups on the multimodal data includes: selecting longitudinal time point data; fitting a model to the longitudinal time point data using one or more of linear modelling, quadratic modelling, and nonlinear modelling; clustering latent growth parameters; and selecting the person as one of the good recovery potential, the moderate recovery potential, and the poor recovery potential.

The computer further analyzes the multimodal data and displays a graph of Functional Independence Measure (FIM) cognitive score on a Y-axis versus time on an X-axis for the person.

The computer further analyzes the multimodal data and generates a model that predicts the functional recovery of the person and includes latent variables of intercept and slope that capture trends of the functional recovery.

The computer further analyzes the multimodal data of persons recovering from the brain injury and clusters groups of the persons based on cognitive data of the persons, mental data of the persons, social data of the persons, and physiological trajectories that generate latent growth parameters based on individual trend.

The computer analyzes the multimodal data over multiple intervals that include 72 hours after the brain injury of the person, one month after the brain injury of the person, three months after the brain injury of the person, six months after the brain injury of the person, and one year after the brain injury of the person.

Advantageous Effects of Invention

The multimodal data includes one or more of Fugl Meyer Assessment of Motor Recovery of the person, Berg Balance Scale (BBS) of the person, a walking test of the person, Mini-Mental State Examination (MMSE) of the person, physiological assessment of the person using EMG and motion sensors, and Functional Independence Measure (FIM) of the person.

The multimodal data can also include one or more of a physiological record of the person, a magnetic resonance imaging (MRI) of the brain of the person, rehabilitation records of the person, and demographic data of the person.

The rehabilitation records can further include one or more of longitudinal assessments by a therapist of a physical condition of the person, a mental condition of the person, and neurological states of the person.

The functional recovery includes both short-term functional recovery for the person from the brain injury and long-term functional recovery for the person from the brain injury.

BRIEF DESCRIPTION OF DRAWINGS

The accompanying figures, where like reference numerals refer to identical or functionally similar elements throughout the separate views and which together with the detailed description below are incorporated in and form part of the specification, serve to illustrate various embodiments and to explain various principles and advantages in accordance with present embodiments.

FIG. 3 is a table showing baseline clinical data and longitudinal monitoring of rehabilitation assessments of the person in accordance with an example embodiment.

FIG. 15 is a model showing a few variables for longitudinal heterogeneous trajectory analysis, separate heterogeneous groups, and prediction of functional recovery in accordance with an example embodiment.

Figure 1:
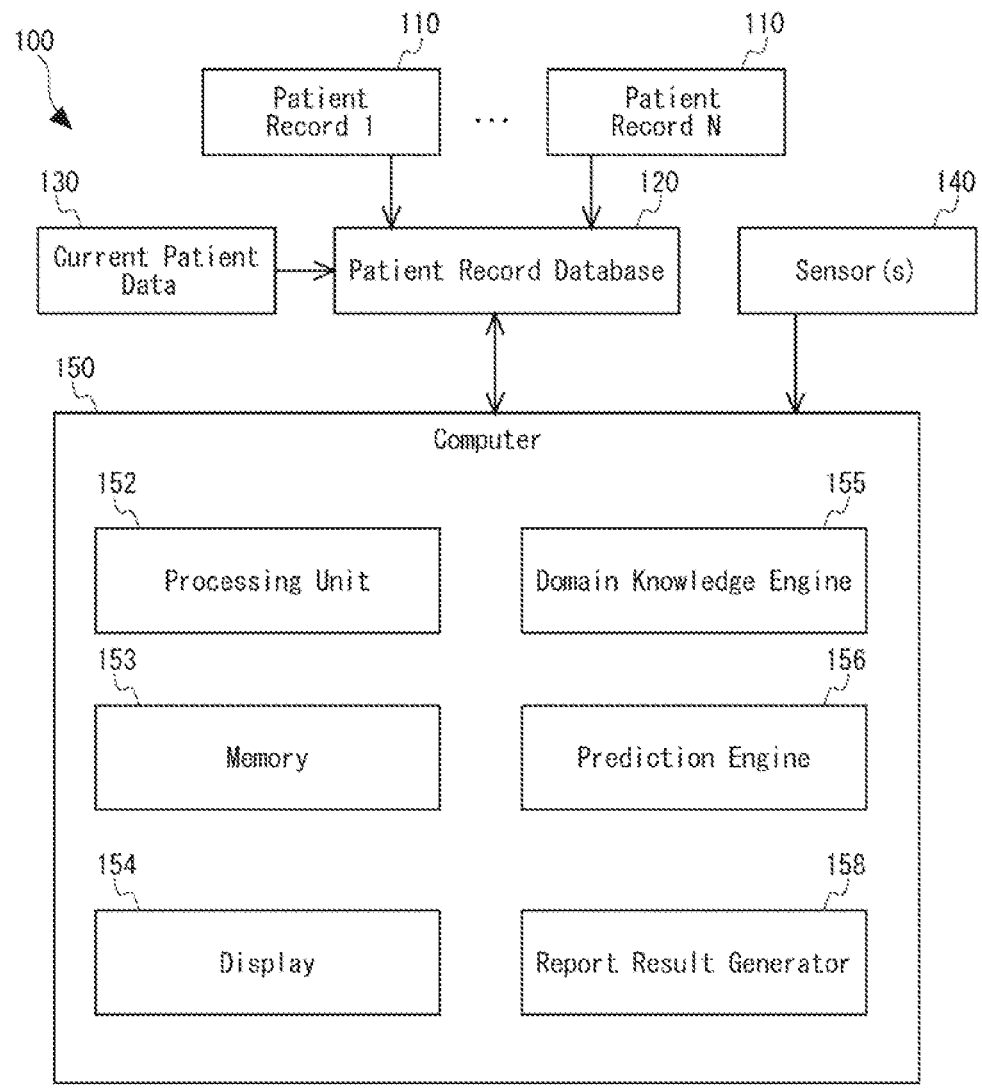
FIG. 1 is a computer system that predicts functional and cognitive recovery of a person after the person suffers from a brain injury in accordance with an example embodiment.

Skilled artisans will appreciate that elements in the figures are illustrated for simplicity and clarity and have not necessarily been depicted to scale.

DESCRIPTION OF EMBODIMENTS

The following detailed description is merely exemplary in nature and is not intended to limit the invention or the application and uses of the invention. Furthermore, there is no intention to be bound by any theory presented in the preceding background of the invention or the following detailed description. It is the intent of the present embodiment to present unique systems and methods for predicting functional and cognitive recovery of a person or patient from a brain injury.

Predicting functional and cognitive recovery of a person after the person suffers from a brain injury (such as a stroke) is a difficult task. Conventional techniques solve this problem by using multilevel regression and similarity matching to make these predictions. These predictions are based on the premise that patient outcomes are considered a homogeneous effect of the recovery journey of the patient. Furthermore, these conventional techniques utilizing multiple regression analysis are based on fixed coefficients. For example, some conventional techniques use similarity matching based on single time point measurements.

Conventional techniques based on the homogeneous effect of patient's recovery are misguided and inherently prone to error. A patient's recovery from a brain injury is heterogeneous since outcomes for patients are based on many factors that are specific or unique to the individual patient. Conventional techniques that utilize multilevel regression and similarity matching in predicting patient outcomes from brain injuries cannot identify unobserved heterogeneity effects of the recovery journal of individual patient.

Example embodiments in accordance with the invention solve these problems with conventional techniques. Such example embodiments provide systems and methods that predict patient's recovery from a brain injury based on identifying unobserved heterogeneous effects of individual patient's recovery trajectories using multimodal longitudinal mixture analysis. Example embodiments include providing mind-cognitive-body function and health relationship models that predict functional and cognitive recovery of the patient.

Example embodiments utilize a more comprehensive set of data to predict the outcome of patients suffering from a brain injury. This multimodal data includes social, cognitive, mental, functional, and physiological. Utilization of such multimodal data enables example embodiments to more accurately predict recovery at an earlier stage of the patient's recovery journey.

Furthermore, example embodiments are not static in making assessments and predictions. Instead, example embodiments develop assessments and predictions that change over time as data is periodically or continually collected during the recovery period of the patient. This data, for example, can be collected at different intervals of time after the injury, such as one or more of 2-3 days after admission, one week, two weeks, one month, two months, three months, four months, five months, six months, etc. up to one year and longer.

Knowledge about factors that determine final outcome of activities after brain injury is important for early rehabilitation management in order to set adequate rehabilitation goals, enable early discharge planning, and to inform patients and relatives correctly. Besides, the ability to live independently after brain injury depends largely on a person's functional abilities and mental and cognitive abilities as well. Therefore, example embodiments include the consideration of various factors, such as cognitive, mental and physiological conditions to accurately assess and predict the functional abilities of the patient. This accurate assessment assists rehabilitation planning and supports realistic goal setting by clinicians and patients. Besides, it is important to understand the current patients' functional recovery level to provide suitable treatment strategies.

FIG. 1 is a computer system 100 that predicts functional and cognitive recovery of a person after the person suffers from a brain injury in accordance with an example embodiment.

The computer system 100 includes patient records 100 (shown as patient record 1 to patient record N) coupled to or in communication with a patient record database 120. This database 120 also receives data 130 of the current patient or person for whom a prediction is being performed.

This data 130 includes multimodal data discussed herein and collected before or after the brain injury. For example, this data includes one or more of data relating to demographics, diagnosis, rehabilitation, assessment trends, and physiological data.

A computer 150 couples to or communicates with the database 120 and one or more sensors 140. By way of example, these sensors include, but are not limited to, one or more of motions sensors, electromyography (EMG) sensors, electroencephalography (EEG) sensors, and blood pressure sensors.

The computer 150 includes one or more of a processor or processing unit 152, a memory 153, a display 154, a domain knowledge engine 155, a prediction engine 156, and a report result generator 158.

The processor or processing unit 152 includes one or more of a central processing unit, CPU, microprocessor, microcontrollers, field programmable gate arrays (FPGA), application-specific integrated circuits (ASIC), etc. for controlling the overall operation of memory 153 (such as random access memory (RAM) for temporary data storage, read only memory (ROM) for permanent data storage, and firmware).

The domain knowledge engine 155 and prediction engine include hardware, software, and/or firmware for executing one or more example embodiments, including one or more blocks, graphs, or figures discussed herein.

The report result generator 158 includes generating or providing one or more of the predicted recoveries. Such predictions can be provided, for example, on the display 154, transmitted over a network (e.g., to another electronic device or memory), generated and displayed as written report, graph, chart, plot, etc., provided as a verbal or audible recommendation, or provided in another form to a doctor, healthcare provider, therapist, patient, or other person.

Figure 2:
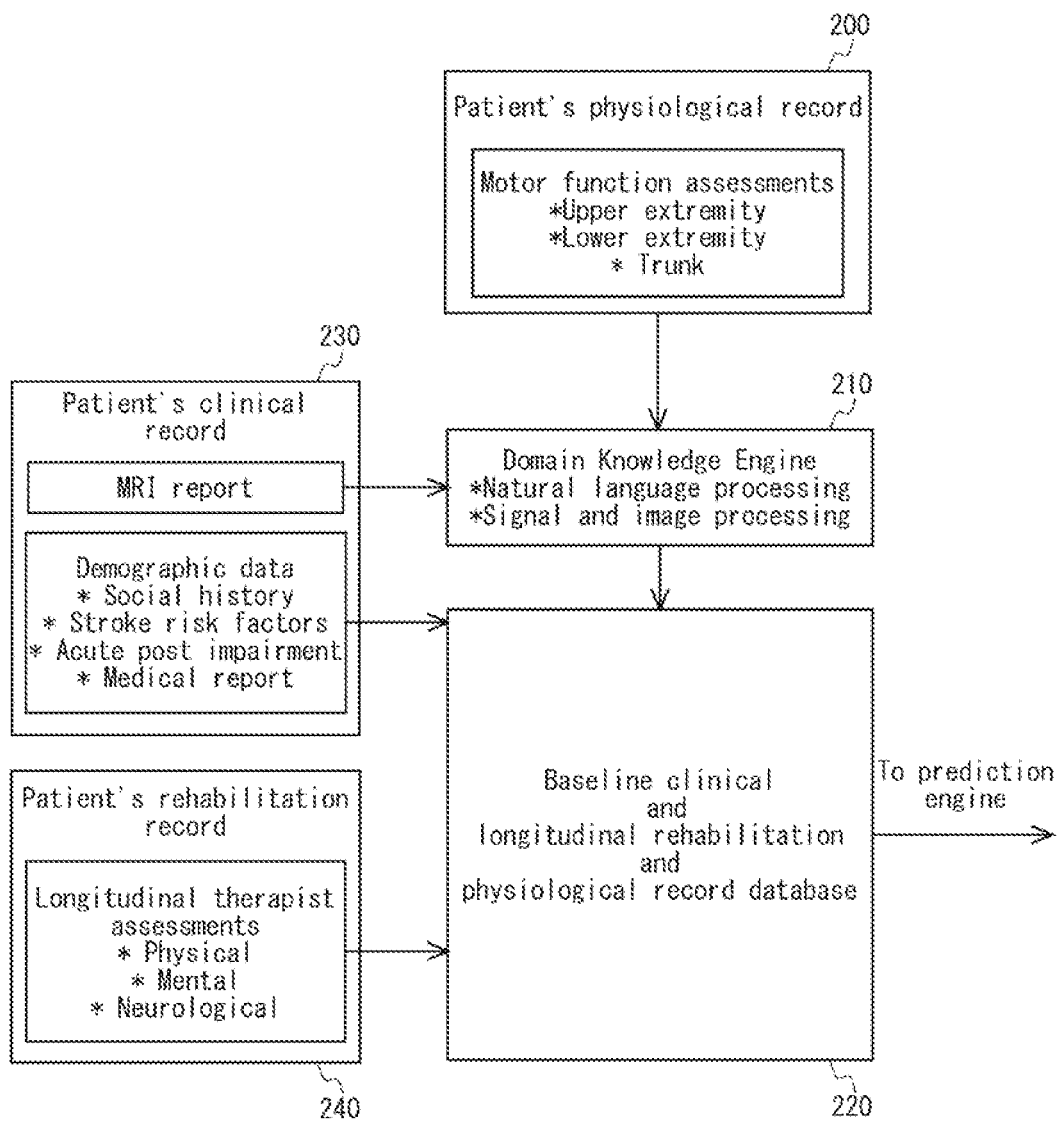
FIG. 2 is a diagram showing flow a multimodal data of the person going to a domain knowledge engine and a record database in accordance with an example embodiment.

FIG. 2 is a diagram showing flow a multimodal data of the person going to a domain knowledge engine and a record database in accordance with an example embodiment.

A patient's physiological record 200 is provided to the domain knowledge engine 210. This record 200 includes, but is not limited to, motor function assessments of the patient, such as upper extremity, lower extremity, and trunk.

The domain knowledge engine 210 can include natural language processing and/or signal and image processing and couples to or communicates with the prediction engine (see prediction engine 156 in FIG. 1) and a baseline clinical and longitudinal rehabilitation and physiological record database 220.

A patient's clinical record 230 is provided to the domain knowledge engine 210 and the database 220. For example, a magnetic resonance imaging (MRI) report is provided to the domain knowledge engine 210 and demographic data is provided to the database 220. By way of example, the patient MRI report could relate to a stroke in which the patient experienced a right cerebellar, small non-hemorrhagic acute infarct in the right cerebellum. By way of example, this demographic data includes one or more of data relating to social history of the patient, stroke risk factors of the patient, acute post impairment of the patient, and medical reports of the patient.

A patient's rehabilitation record 240 is provided to the database 220. By way of example, this record includes longitudinal assessments made by therapists, such as assessments pertaining to physical condition of the patient, mental condition of the patient, and neurological condition of the patient.

FIG. 3 is a table 300 showing baseline clinical data and longitudinal monitoring of rehabilitation assessments of the person in accordance with an example embodiment.

The table 300 includes two columns: statistical data fields and dynamic data fields for monitoring recovery. The statistical data fields further include data on admission and data on discharge. The data on admission includes one or more of Age, Gender, Height, Weight, BMI, Ethnicity, Education, Marital status, Social support, Employment status, Alcoholism consumption, Smoking behavior, Blood pressure, Some comorbidity, such as hypertension, heart, kidney disease, Blood supply, Lesion, Location of the brain, ICH volume, IVH, Infratentorial ICH, Impairments, Side affected, Limbs affected part, MRI result, Complications, GCS, Modified Rankin Scale, and NIHSS score.

The data on discharge includes one or more of discharge date, premorbid ADL, premorbid IADL, discharge destination, discharge ADL, discharge IADL, discharge social issues, discharge gait, discharge level of assistance, and length of stay.

The dynamic data fields for monitoring recovery include one or more time points after the brain injury. Such time points include, but are not limited to, one or more of 2-3 days after admission, one week, two weeks, three weeks, one month, two months, three months, four months, five months, six months, one year, or longer.

The dynamic data includes one or more of Fugl Meyer Assessment of Motor Recovery, Berg Balance Scale (BBS), Lawton IADL, six-minute walk test (6 MWT), ten-meter walk test, trunk impairment scale, mini-mental state examination (MMSE), mood_depression, mood_anxiety, mood_stress, patient health questionnaire-4 for feeling, social activity, physiological assessment using EMG and motion sensors, and Functional Independence Measure (FIM).

Figure 4:
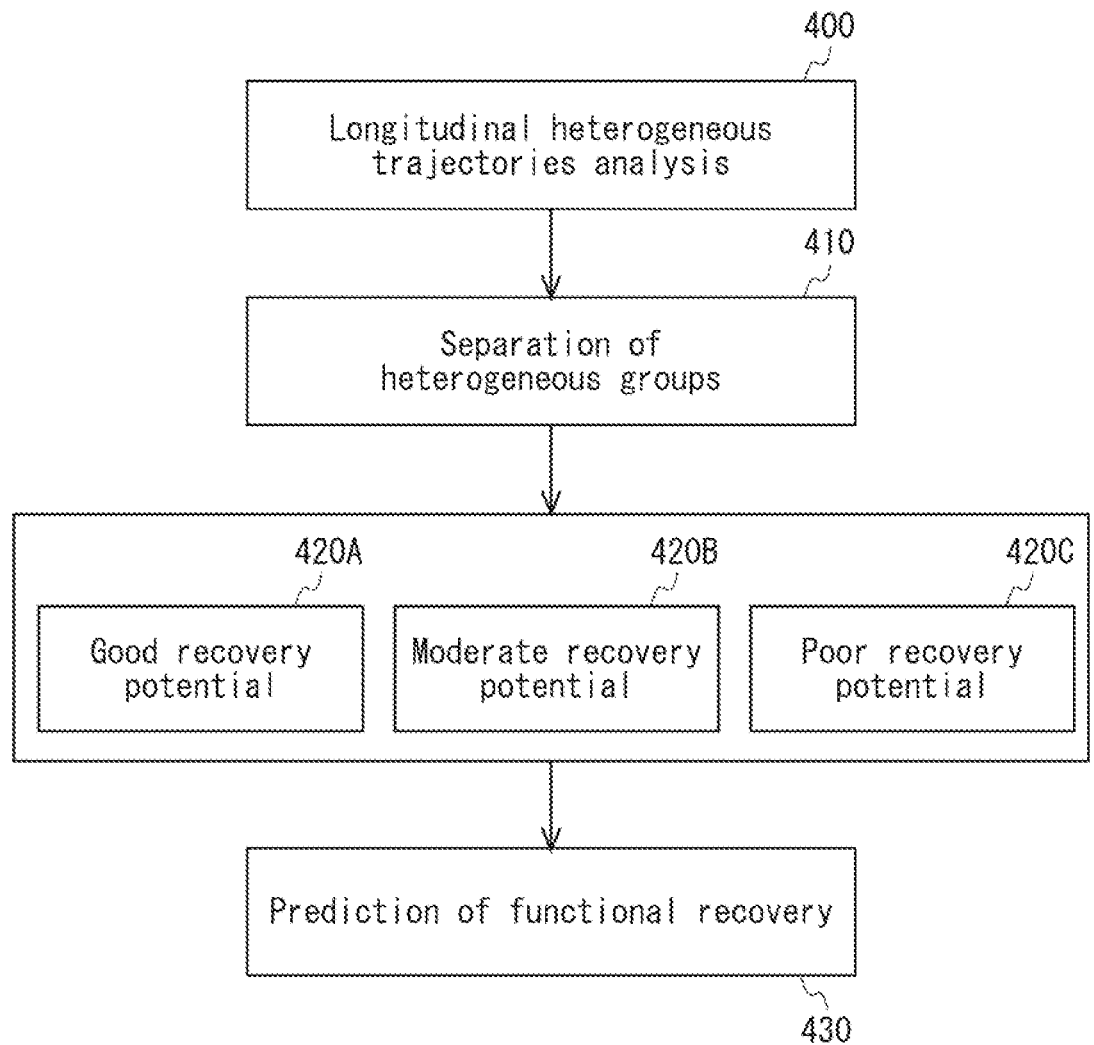
FIG. 4 is a method to predict functional recovery of a person after the person suffers from a brain injury in accordance with an example embodiment.

FIG. 4 is a method to predict functional recovery of a person after the person suffers from a brain injury in accordance with an example embodiment.

By way of example, the method shows flow of the prediction engine. This flow utilizes multidimensional longitudinal heterogeneous trajectory analysis with time varying and invariant predictors and outcomes.

Block 400 includes execution of longitudinal heterogeneous trajectories analysis. This block can be a first step or first process in the method.

Block 410 includes execution of separation of heterogeneous groups. This block can be a second step or second process in the method. Separation of the heterogeneous groups includes separating patient potential into one more categories. Such categories include, but are not limited to, good recovery potential 420A, moderate recovery potential 420B, and poor recovery potential 420C.

Block 430 includes prediction of functional recovery of the patient suffering from a brain injury. This block can be a third step or third process in the method.

Figure 5:
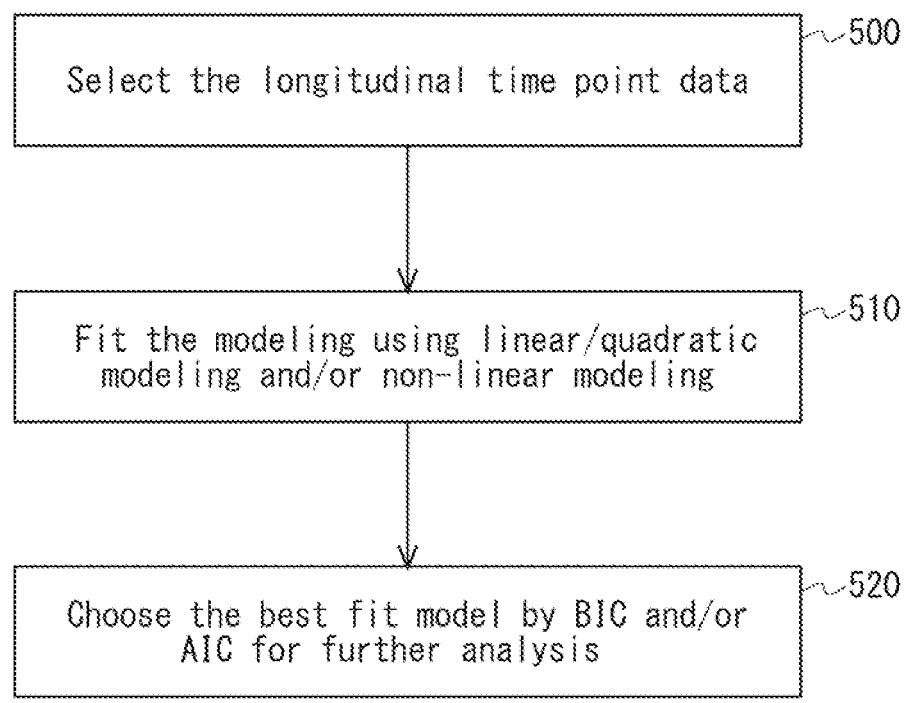
FIG. 5 is a method executing longitudinal heterogeneous trajectory analysis in accordance with an example embodiment.

FIG. 5 is a method executing longitudinal heterogeneous trajectory analysis in accordance with an example embodiment. FIG. 5 shows block 400 of FIG. 4 in more detail (i.e., execution of longitudinal heterogeneous trajectories analysis).

Block 500 includes select the longitudinal time point data from one or more longitudinal assessment and physiological data. For example, the longitudinal time point data includes, but is not limited to, two or more of available time point data such as 2-3 days from admission, 1 week and 2 weeks, one month, 3 months of ADL, IADL, MMSE and etc.

Block 510 includes fit the model using linear/quadratic modelling and/or nonlinear modelling. First, linear model fitting of provided longitudinal time point data was performed using intercept and slope of individual patient longitudinal data. Then, different types of model fittings were performed such as quadratic model fit or exponential fitting.

Block 520 includes choose the best fit model by Bayesian information criterion (BIC) and/or Akaike information criterion (AIC) for further analysis. In this step, the BIC and/or AIC are computed for performed model fit from the Block 510 and select the model that gives a minimum BIC/AIC for the best model fit on the selected longitudinal time point data.

Figure 6:
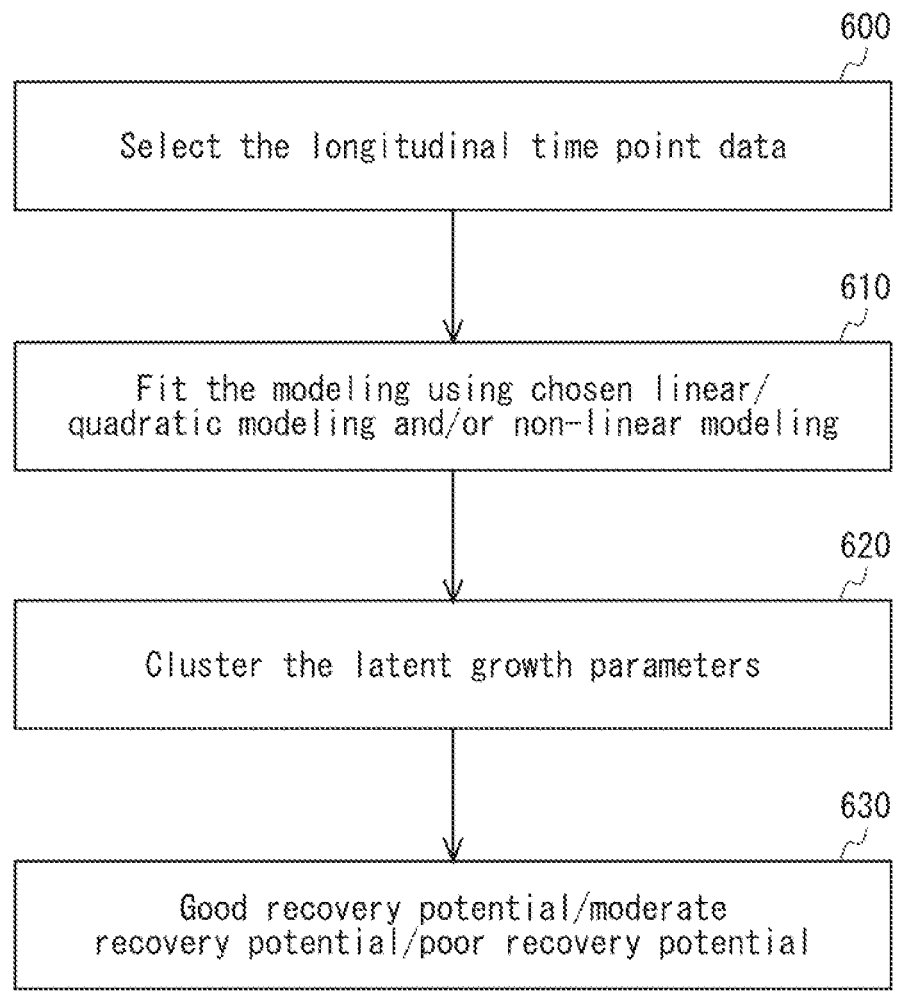
FIG. 6 is method executing separation of heterogeneous groups in accordance with an example embodiment.

FIG. 6 is a method executing separation of heterogeneous groups in accordance with an example embodiment. FIG. 6 shows block 410 of FIG. 4 in more detail (i.e., execution of separation of heterogeneous groups).

Block 600 includes select the longitudinal point time data. The longitudinal time point data are from one or more longitudinal assessment and physiological data. For example, the longitudinal time data includes, but is not limited to, two or more of available time point data such as 2-3 days from admission, 1 week and 2 weeks, one month, 3 months of ADL, IADL, MMSE and etc. It is similar step with Block 500.

Block 610 includes fit the model using linear/quadratic modelling and/or nonlinear modelling. In this step, Model fitting was performed based on the result of Blok 520 which gave the best model fit according to the models that performed in Block 510.

Block 620 includes cluster the latent growth parameters. The clustering was performed using one of the clustering methods such as hierarchical clustering, K-means clustering and Expectation-Maximization (EM) clustering using Gaussian Mixture Models (GMM), and so on.

Block 630 includes identification of the patient into one of a good recovery potential, a moderate recovery potential, and a poor recovery potential.

Example embodiments provide a modelling technique that includes multidimensional longitudinal heterogeneous trajectories analysis with time varying and invariant predictors and outcomes. The modelling technique provides advantages over conventional techniques. For example, the modelling techniques in accordance with an example embodiment capture non-observed heterogeneity trajectories of recovery trend among patient that may exist in the population (e.g., patterns of subjects linked to an unknown behavior/disease risk). The modelling techniques also capture latent variables (intercept, slope) of individual trend of the patient. Furthermore, the modelling technique generates a cluster group of patients based on individual type of cognitive, mental, social and physiological trajectory that generate latent growth parameters based on individual trend.

Modelling techniques in accordance with example embodiments further generate or predict patterns of recovery, such as for multiple time point predictions and single time point predictions. Such predictions show mediation effects on different factors for individual patient, such as depression effects on functional abilities.

The sample of longitudinal time point of cognitive, physical and physiological assessments, modelling technique and/or sample output generations are shown in FIGS. 7-15.

Figure 7A:
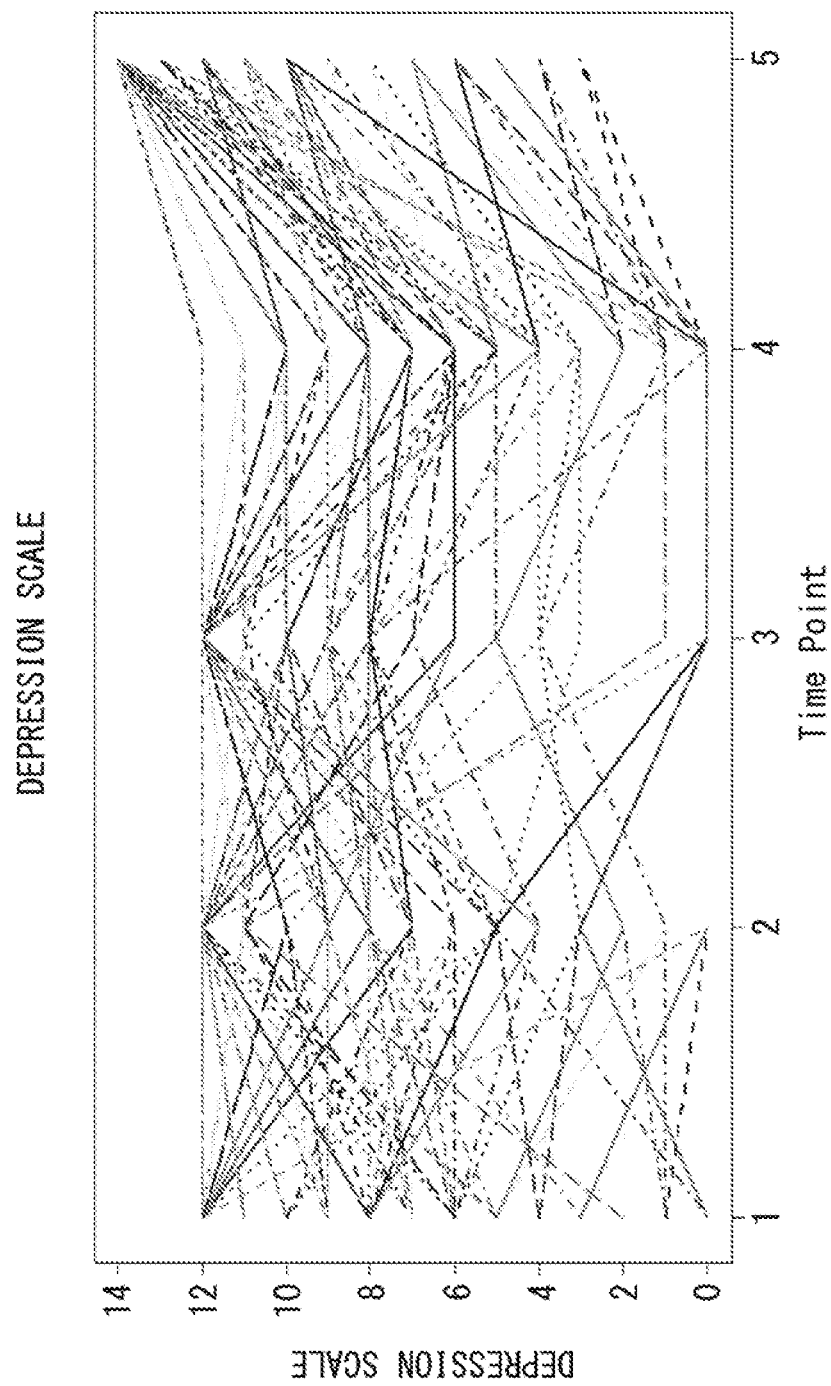
FIG. 7A is a graph of sample trajectories of rehabilitation assessment with depression scale versus time in accordance with an example embodiment.

FIG. 7A is a graph of sample trajectories of rehabilitation assessment with depression scale versus time in accordance with an example embodiment. The Y-axis is a depression scale (ranging from 0 to 14), and the X-axis is time.

Figure 7B:
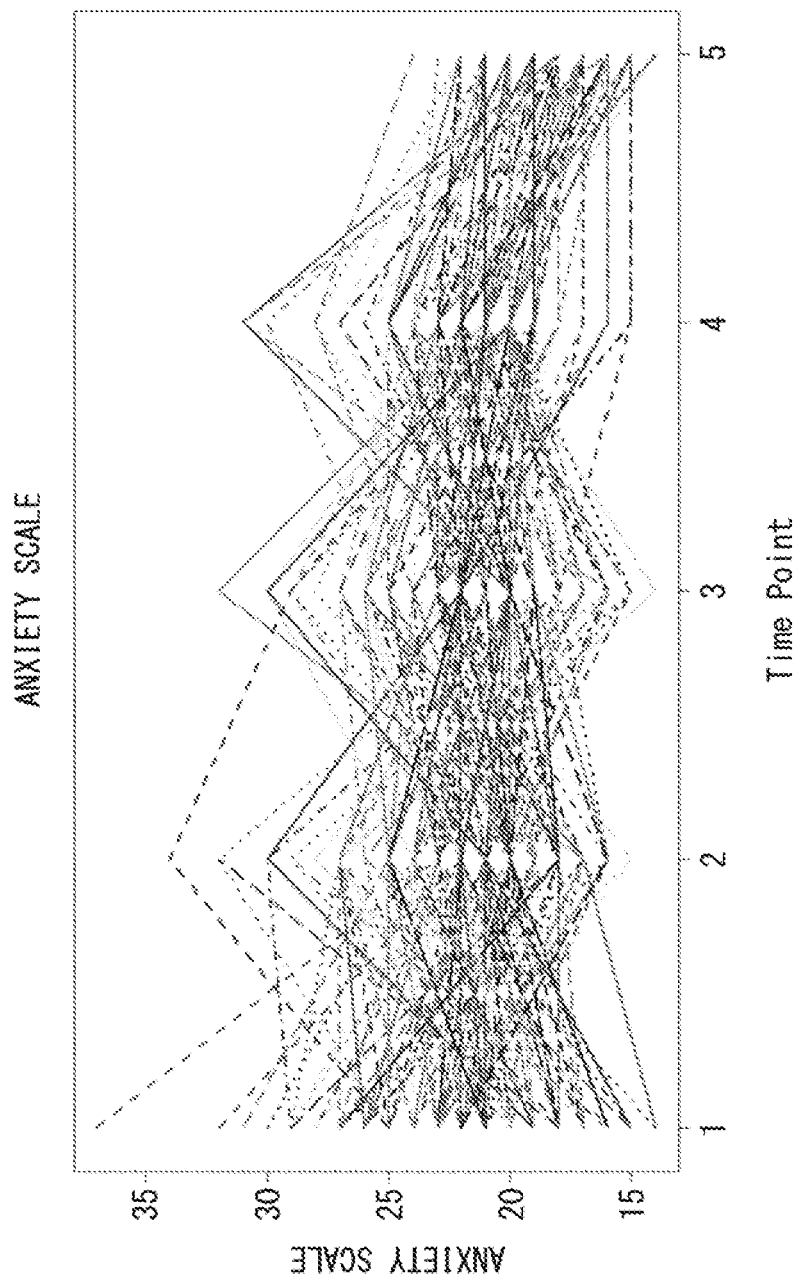
FIG. 7B is a graph of sample trajectories of rehabilitation assessment with anxiety scale versus time in accordance with an example embodiment.

FIG. 7B is a graph of sample trajectories of rehabilitation assessment with anxiety scale versus time in accordance with an example embodiment. The Y-axis anxiety scale ranges from 0 to 35+, and the X-axis is time.

Figure 7C:
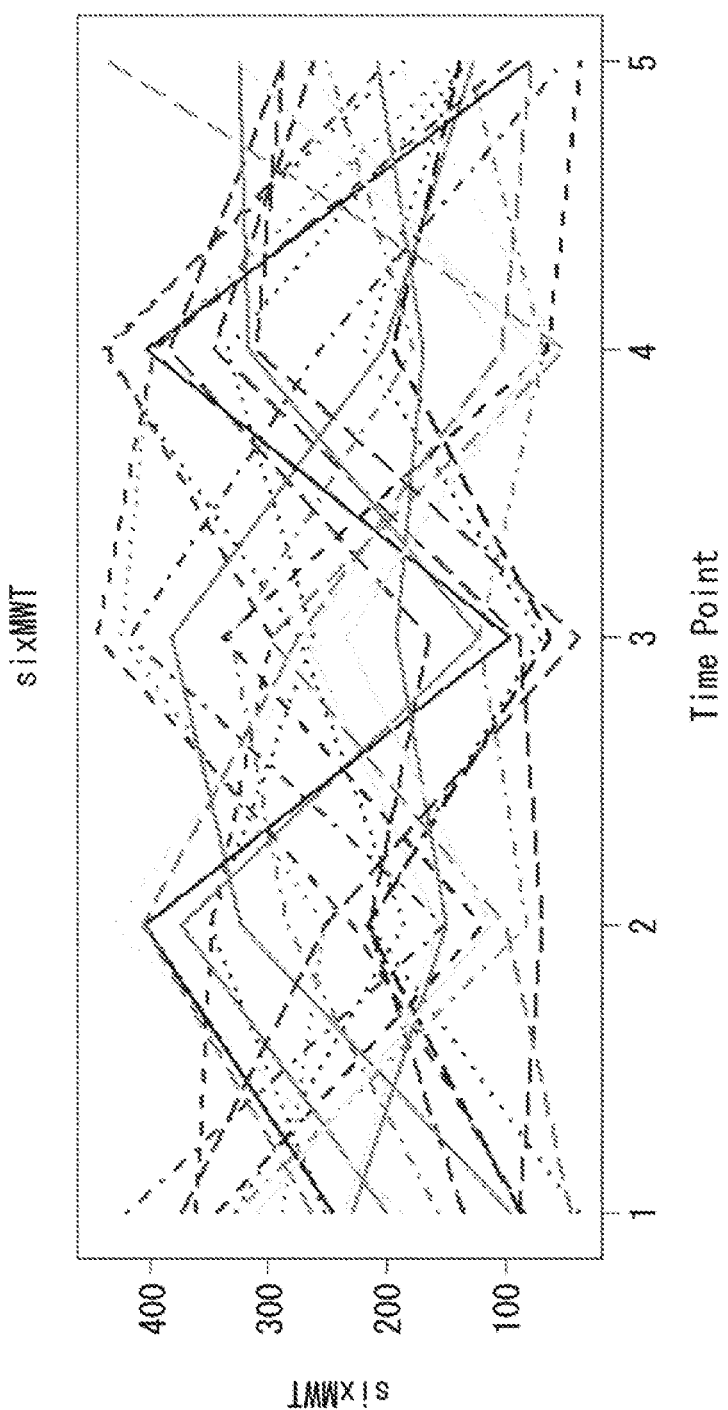
FIG. 7C is a graph of sample trajectories of rehabilitation assessment wide of a six minute walking test (six MWT) in accordance with an example embodiment.

FIG. 7C is a graph of sample trajectories of rehabilitation assessment wide of a six minute walking test (six MWT) in accordance with an example embodiment. The Y-axis ranges from 0 to 400, and the X-axis is time.

Figure 7D:
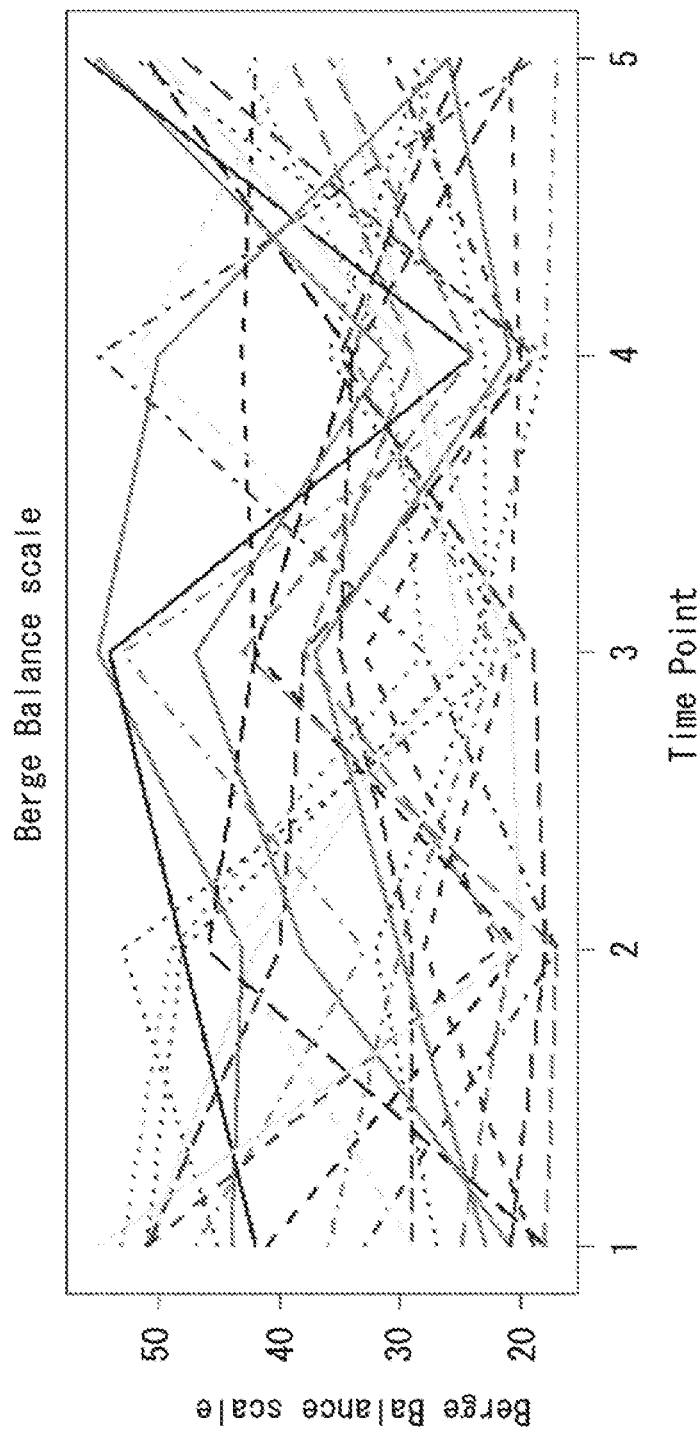
FIG. 7D is a graph of sample trajectories of rehabilitation assessment with Berg balance scale versus time in accordance with an example embodiment.

FIG. 7D is a graph of sample trajectories of rehabilitation assessment with Berg balance scale versus time in accordance with an example embodiment. The Y-axis is Berg Balance scale (ranging from 0 to 50+), and the X-axis is time.

Figure 8A:
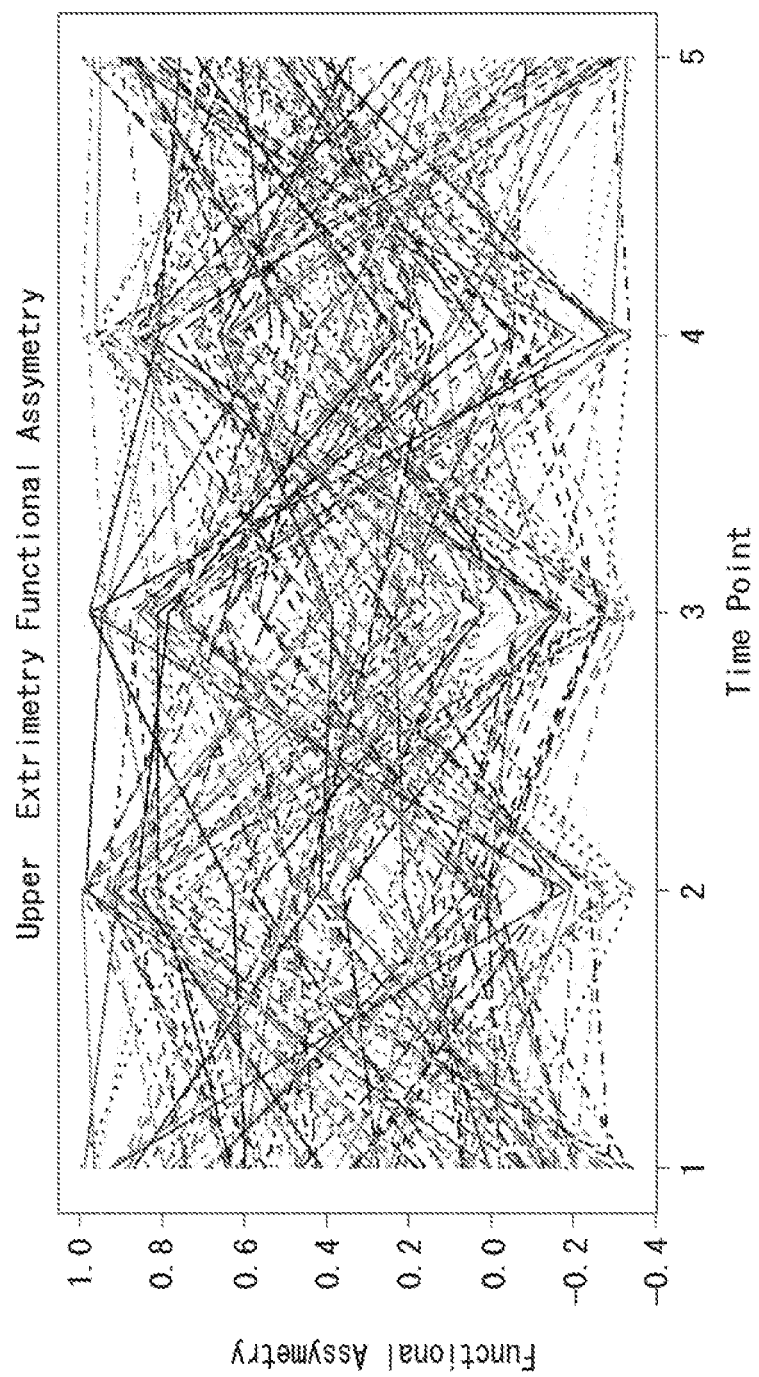
FIG. 8A is a graph of sample trajectories of physiological data of upper extremity functional asymmetry versus time in accordance with an example embodiment.

FIG. 8A is a graph of sample trajectories of physiological data of upper extremity functional asymmetry versus time in accordance with an example embodiment. The Y-axis is functional asymmetry (ranging from −0.4 to 1.0), and the X-axis is time.

Figure 8B:
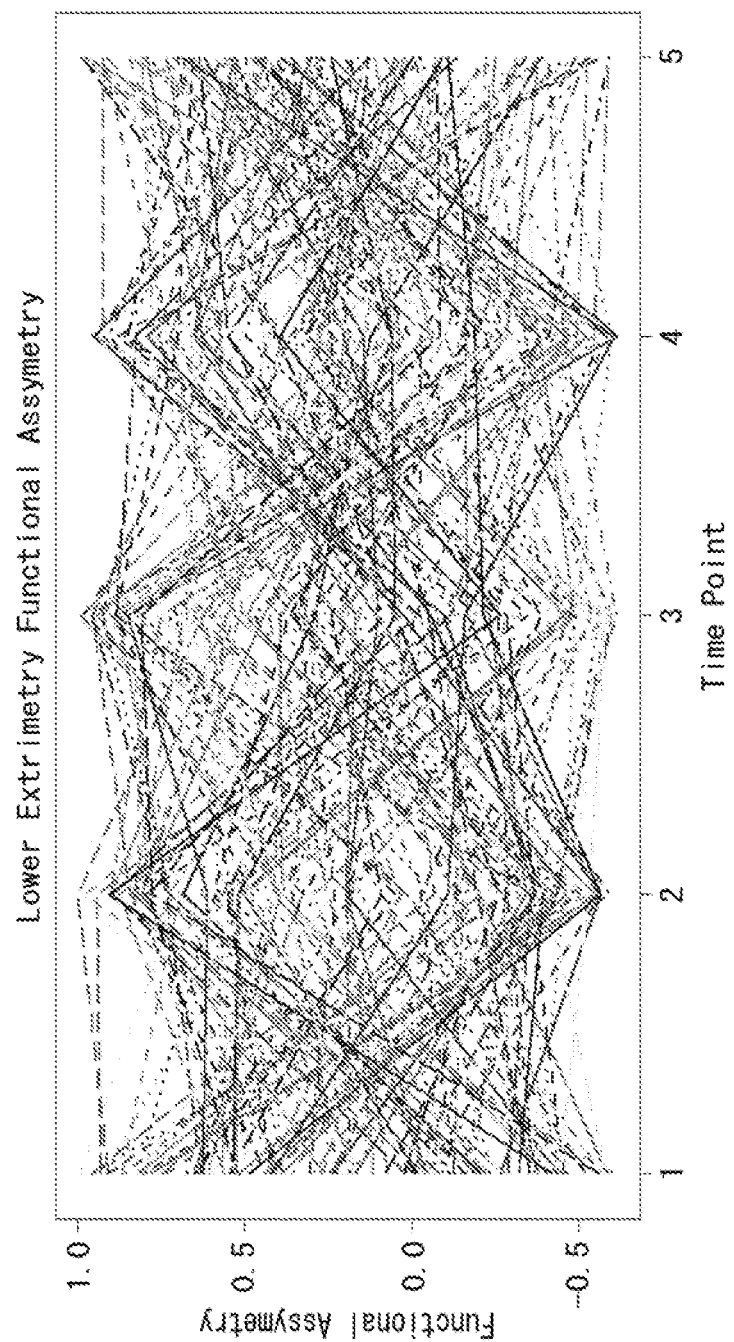
FIG. 8B is a graph of sample trajectories of physiological data of lower extremity functional asymmetry versus time in accordance with an example embodiment.

FIG. 8B is a graph of sample trajectories of physiological data of lower extremity functional asymmetry versus time in accordance with an example embodiment. The Y-axis is functional asymmetry (ranging from about −0.5 to 1.0), and the X-axis is time.

Figure 9A:
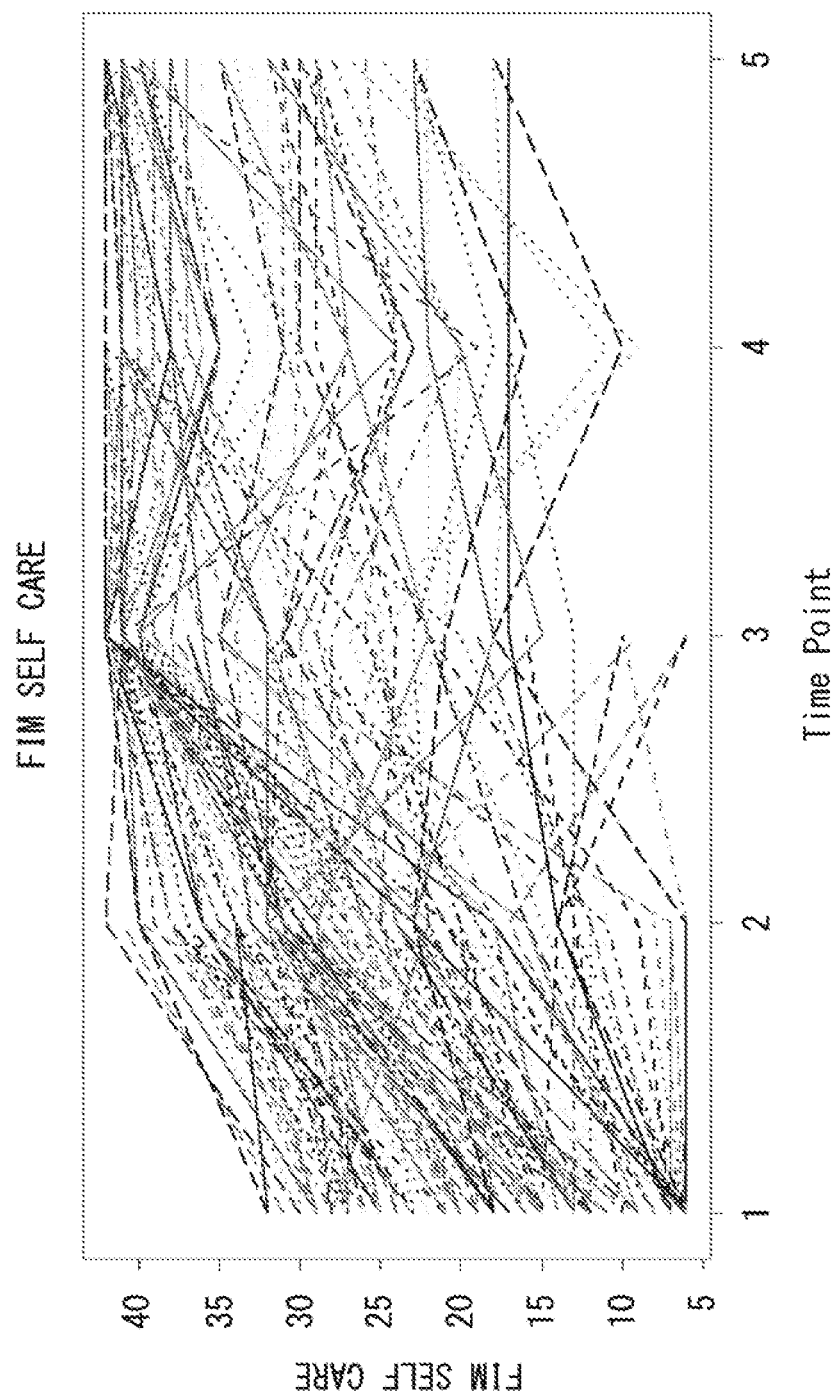
FIG. 9A is a graph of sample trajectories of functional recovery pattern of FIM self-care versus time in accordance with an example embodiment.

FIG. 9A is a graph of sample trajectories of functional recovery pattern of FIM self-care versus time in accordance with an example embodiment. The Y-axis is FIM self-care (ranging from 0 to 40+), and the X-axis is time.

Figure 9B:
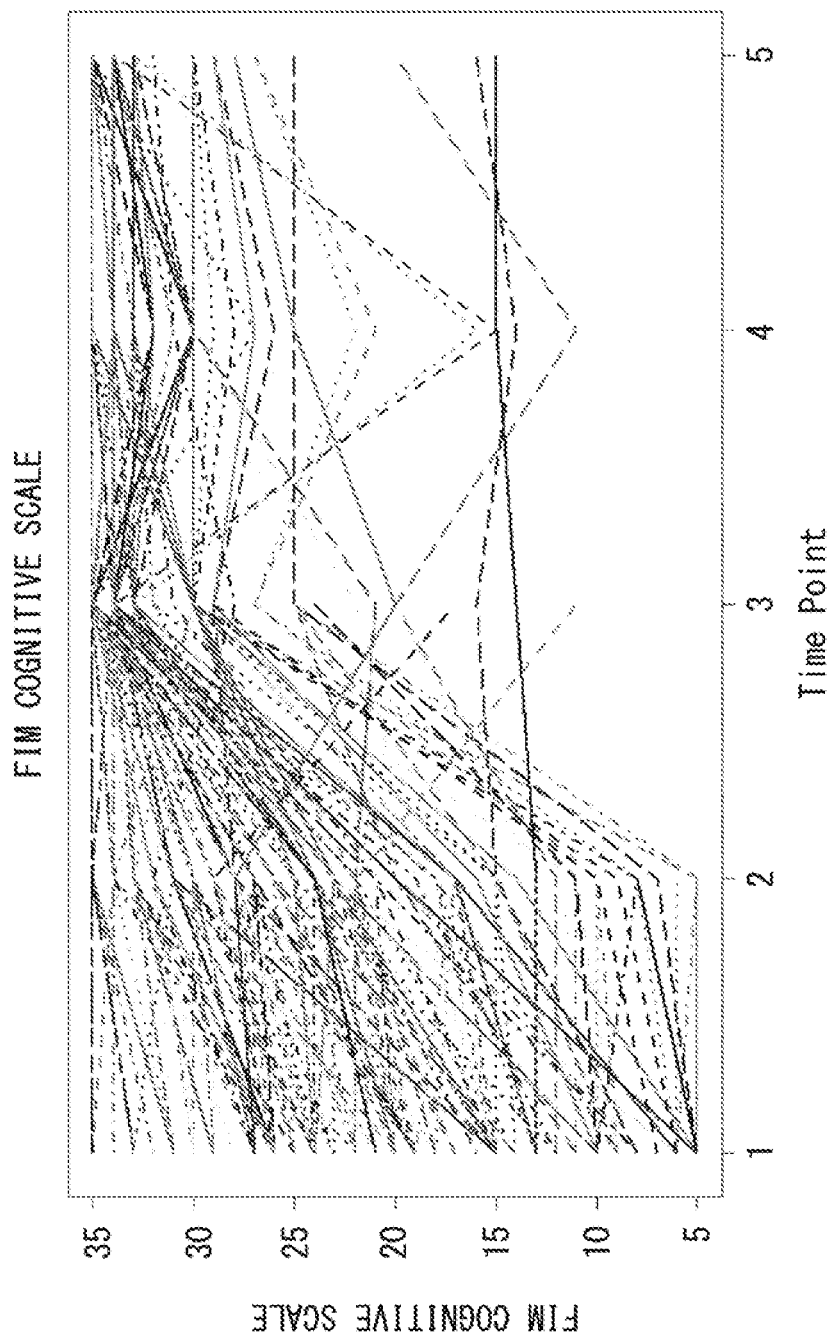
FIG. 9B is a graph of sample trajectories of functional recovery pattern of FIM cognitive scale versus time in accordance with an example embodiment.

FIG. 9B is a graph of sample trajectories of functional recovery pattern of FIM cognitive scale versus time in accordance with an example embodiment. The Y-axis is FIM cognitive scale (ranging from 0 to 35+), and the X-axis is time.

Figure 9C:
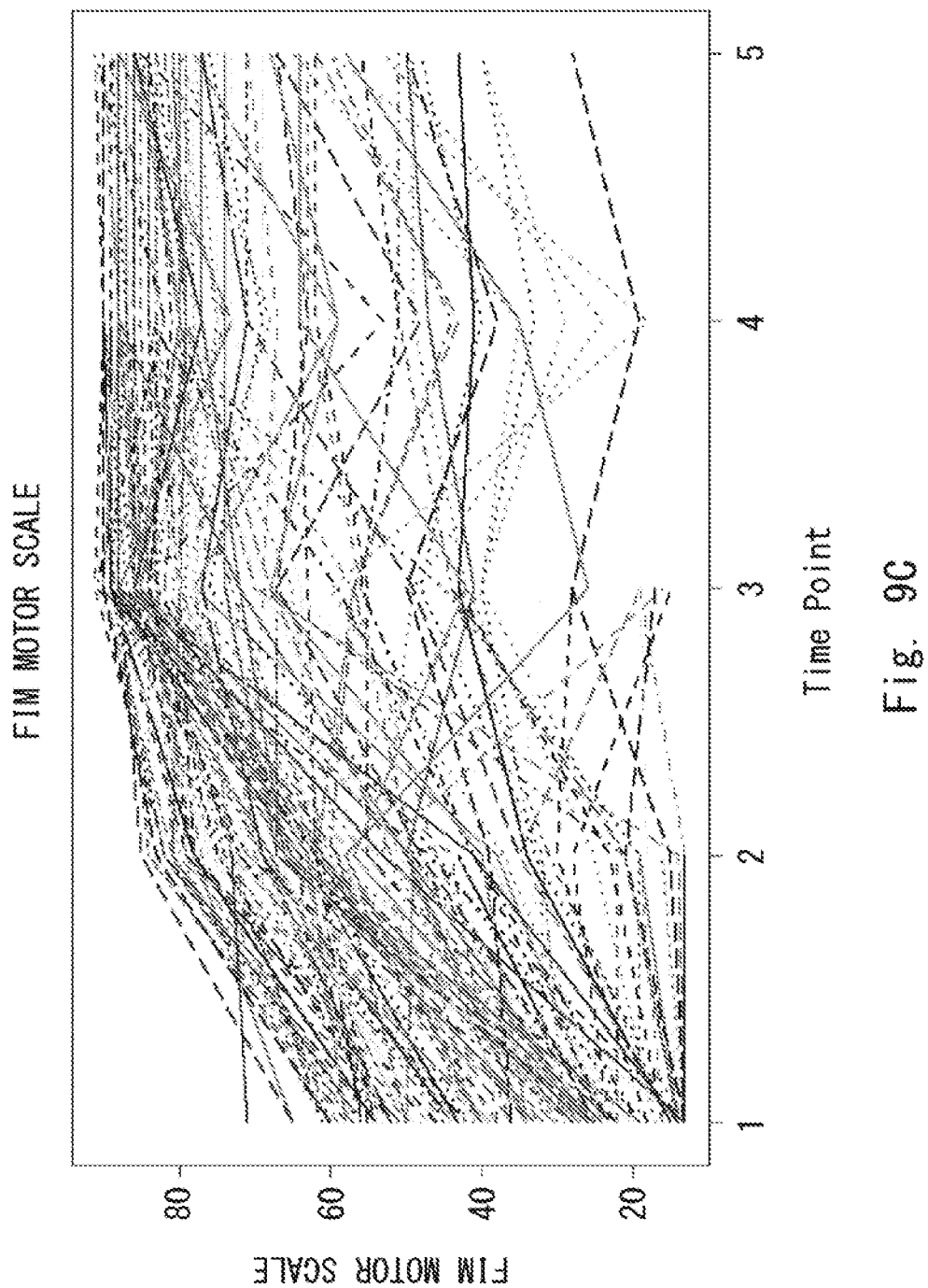
FIG. 9C is a graph of sample trajectories of functional recovery pattern of FIM motor scale versus time in accordance with an example embodiment.

FIG. 9C is a graph of sample trajectories of functional recovery pattern of FIM motor scale versus time in accordance with an example embodiment. The Y-axis is FIM motor scale (ranging from 0 to 80+), and the X-axis is time.

Figure 9D:
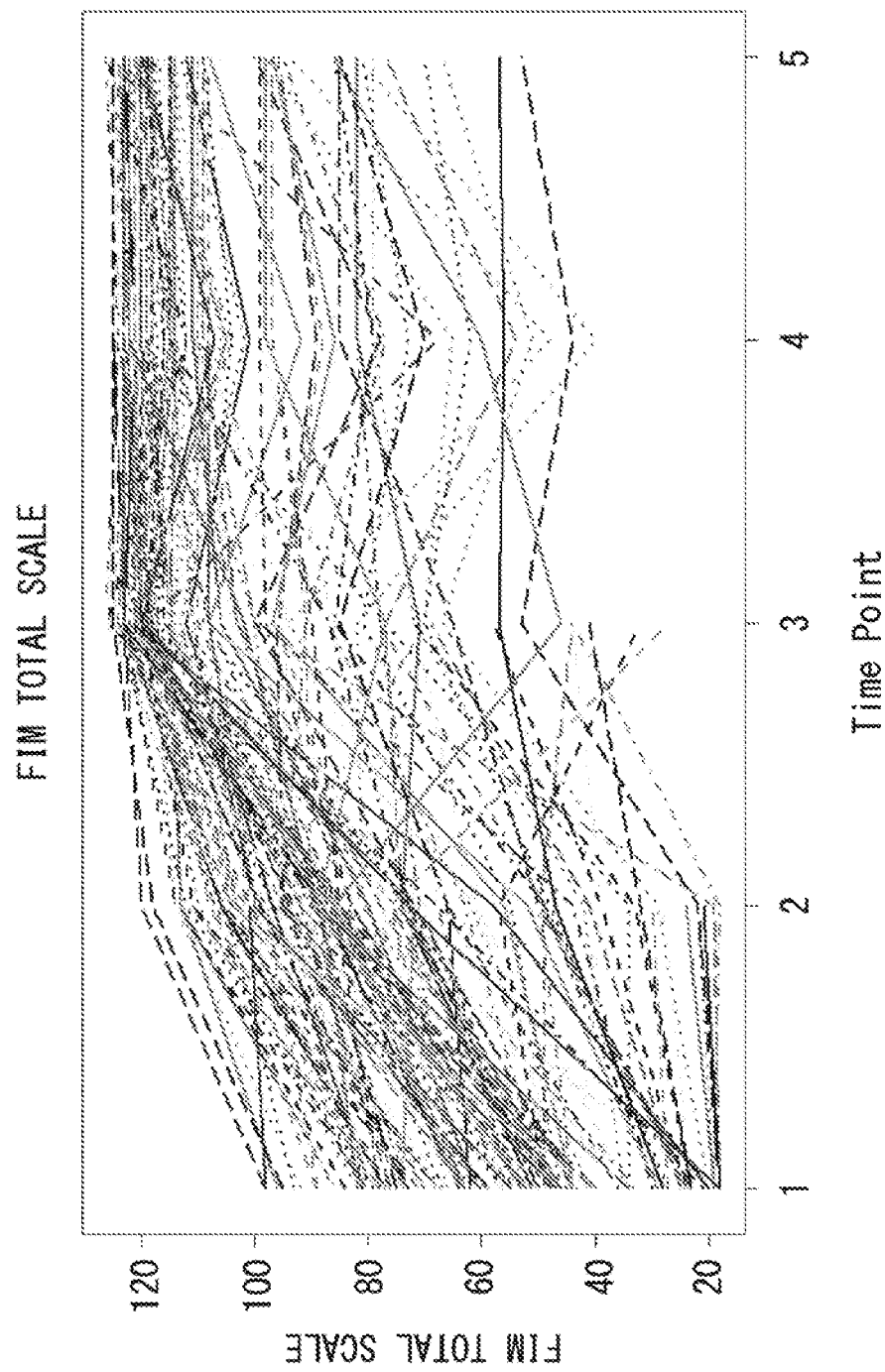
FIG. 9D is a graph of sample trajectories of functional recovery pattern of FIM total scale versus time in accordance with an example embodiment.

FIG. 9D is a graph of sample trajectories of functional recovery pattern of FIM total scale versus time in accordance with an example embodiment. The Y-axis is FIM total scale (ranging from 0 to 120+), and the X-axis is time.

Figure 10A:
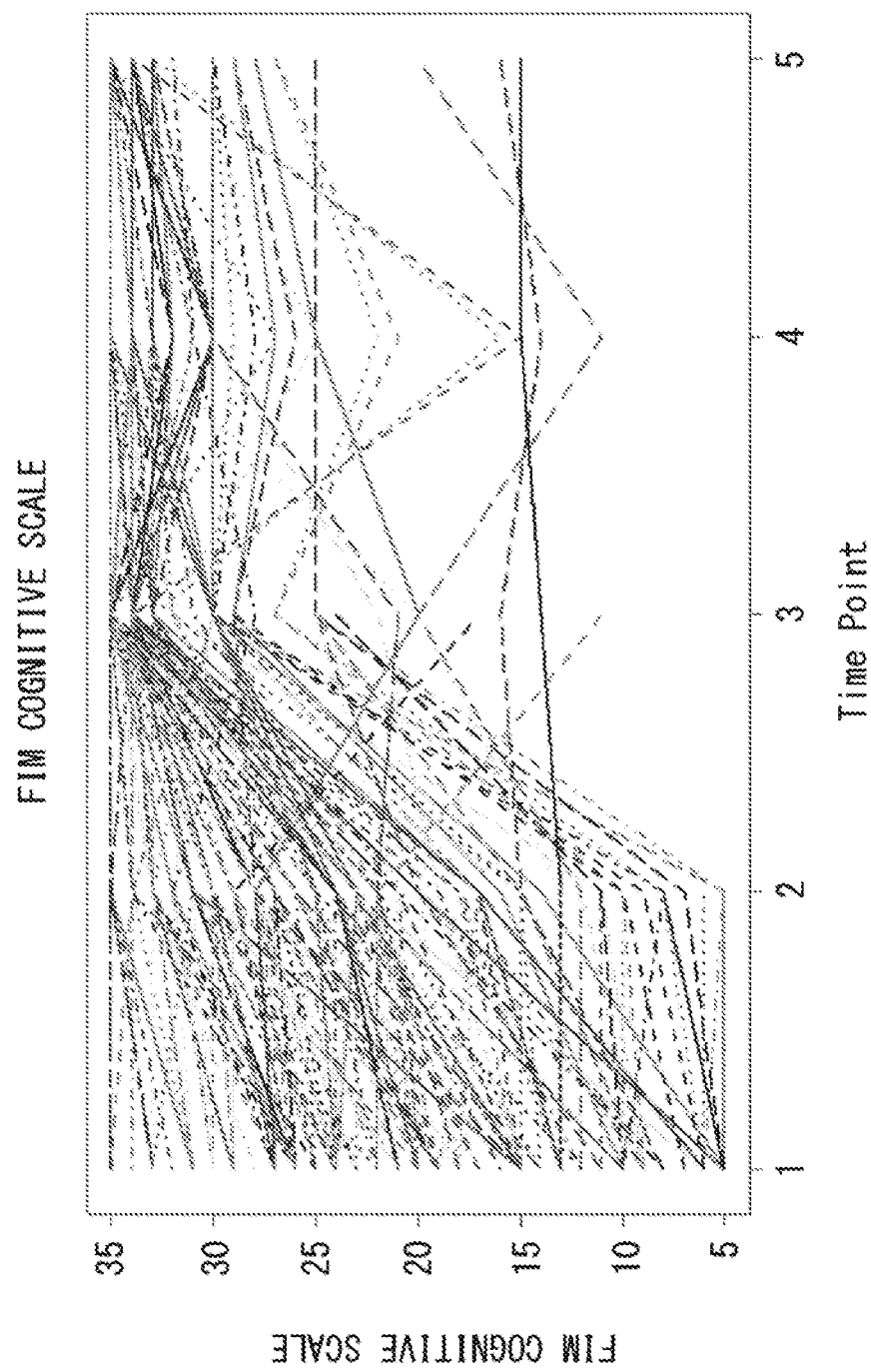
FIG. 10A is a demo of separation of heterogeneous groups as a graph of FIM cognitive scale versus time in accordance with an example embodiment.

FIG. 10A is a demo of separation of heterogeneous groups as a graph of FIM cognitive scale versus time in accordance with an example embodiment. The Y-axis is FIM cognitive scale (ranging from 0 to 35+), and the X-axis is time.

Figure 10B:
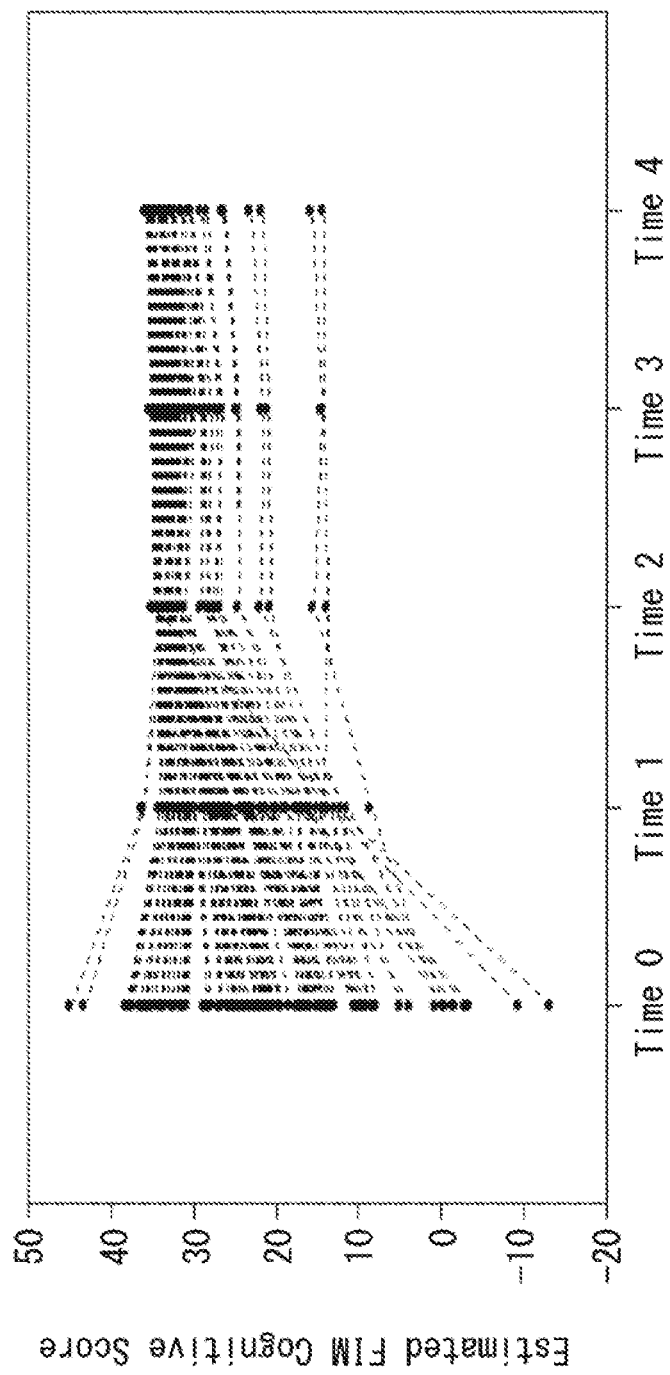
FIG. 10B is a demo of first step of separation of heterogeneous groups as a graph of FIM cognitive score versus time in accordance with an example embodiment.

FIG. 10B is a demo of separation of heterogeneous groups as a graph of FIM cognitive score versus time in accordance with an example embodiment. The Y-axis is FIM cognitive score (ranging from 0 to 36), and the X-axis is time. The data includes estimated means and observed mean of three heterogeneous groups of FIM cognitive score.

Figure 10C:
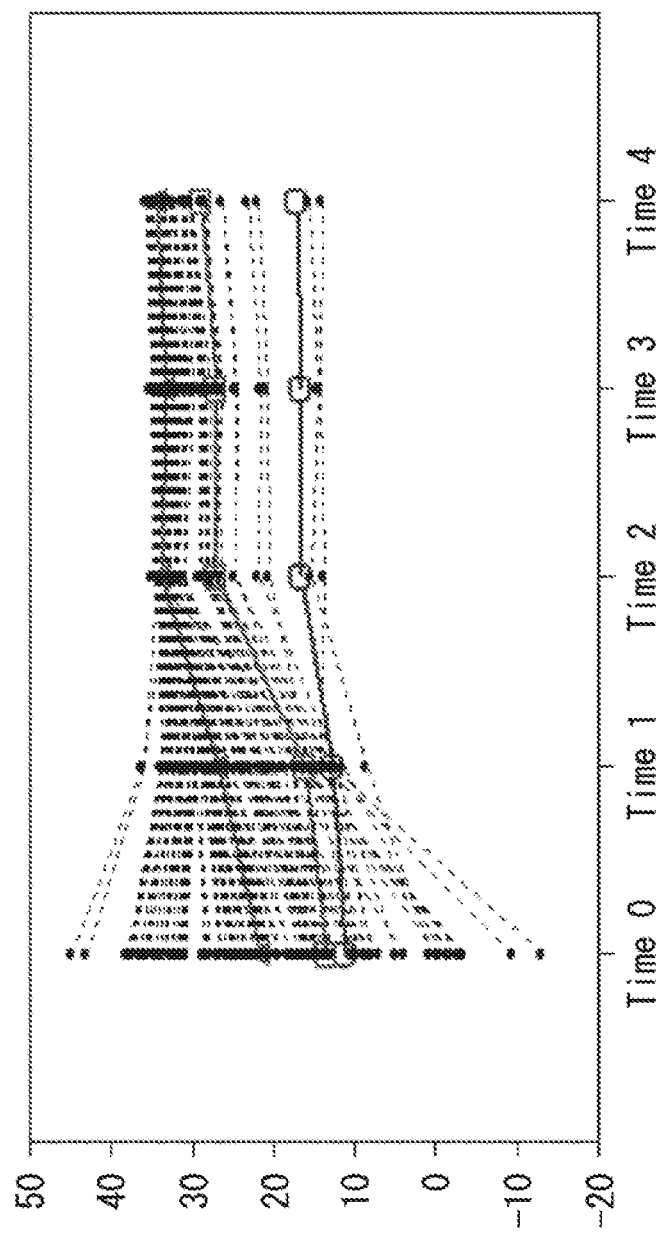
FIG. 10C is a demo of separation of heterogeneous groups as a graph of FIM cognitive score versus time in accordance with an example embodiment.

FIG. 10C is a demo of first step of separation of heterogeneous groups as a graph of FIM cognitive score versus time in accordance with an example embodiment. The Y-axis is FIM cognitive score (ranging from −20 to 50), and the X-axis is time. The data includes estimated individual value of FIM cognitive score based on quadratic model fitting.

Figure 10D:
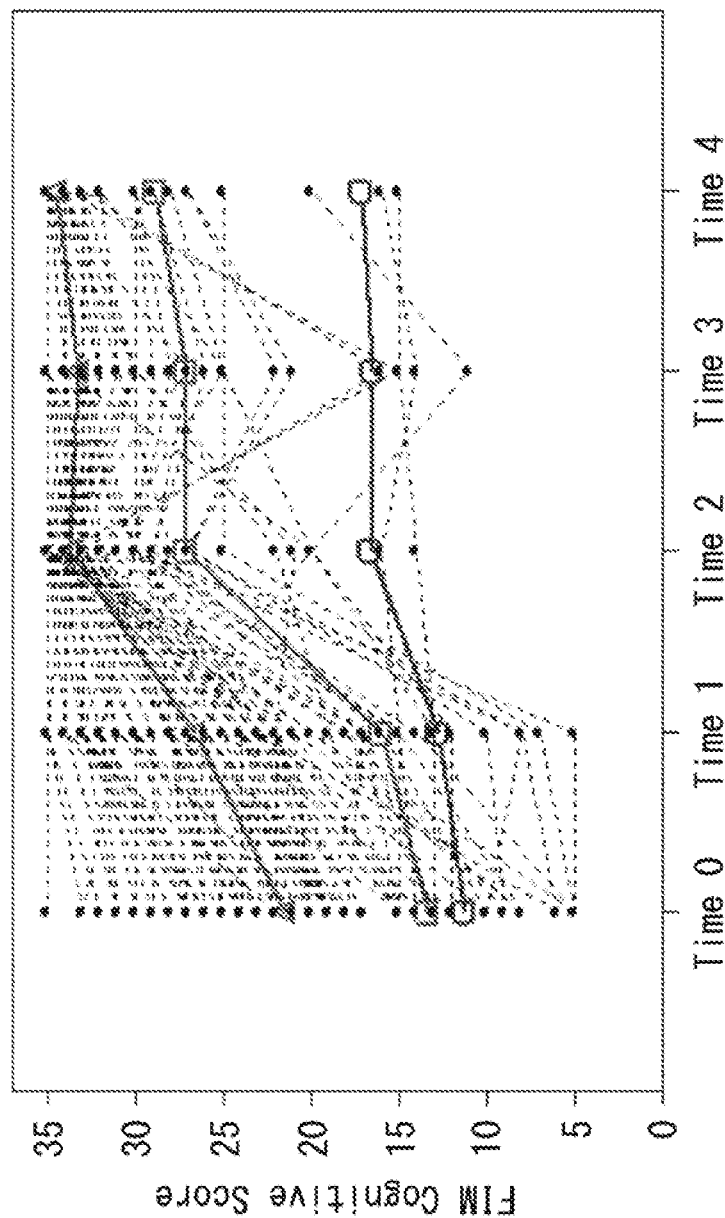
FIG. 10D is a demo of separation of heterogeneous groups as a graph of FIM cognitive score versus time in accordance with an example embodiment.

FIG. 10D is a demo of separation of heterogeneous groups as a graph of FIM cognitive score versus time in accordance with an example embodiment. The Y-axis is FIM cognitive score (ranging from −20 to 50), and the X-axis is time. The data includes estimated mean of three heterogeneous groups and estimated individual value of FIM cognitive score based on quadratic model fitting and.

Figure 10E:
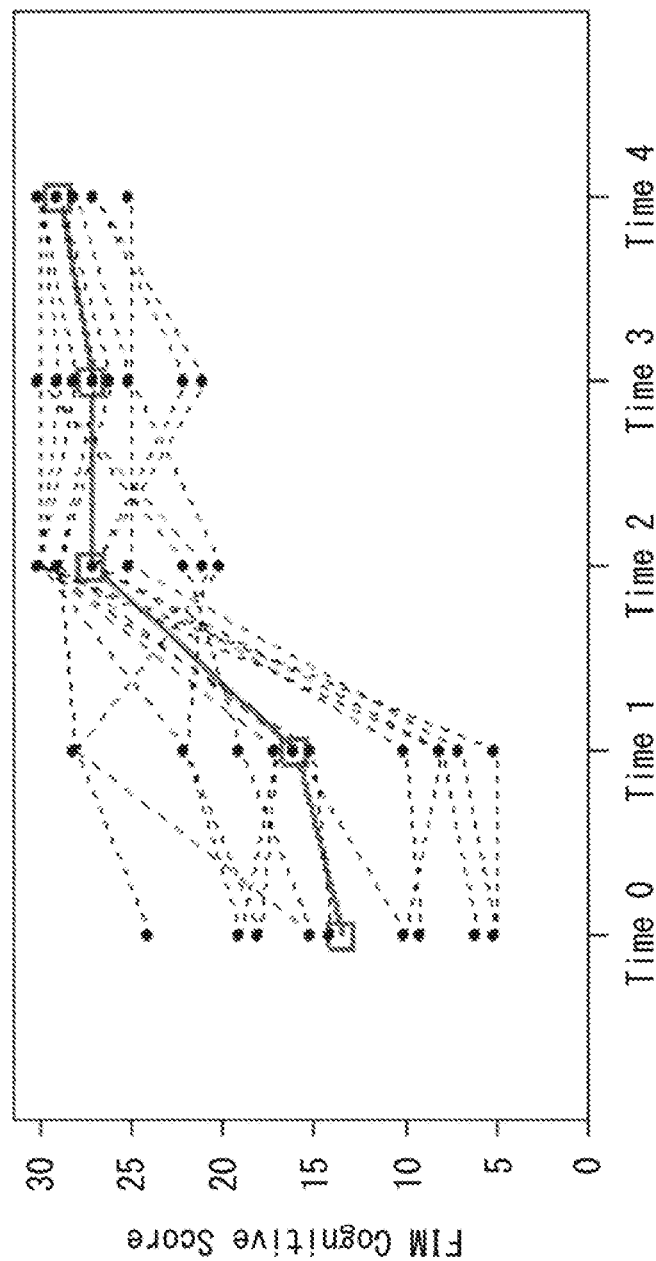
FIG. 10E is a demo of separation of heterogeneous groups as a graph of FIM cognitive score versus time in accordance with an example embodiment.

FIG. 10E is a demo of separation of heterogeneous groups as a graph of FIM cognitive score versus time in accordance with an example embodiment. The Y-axis is FIM cognitive score (ranging from 0 to 35+), and the X-axis is time. The data includes mean value of three heterogeneous groups and observed individual value of FIM cognitive score.

Figure 10F:
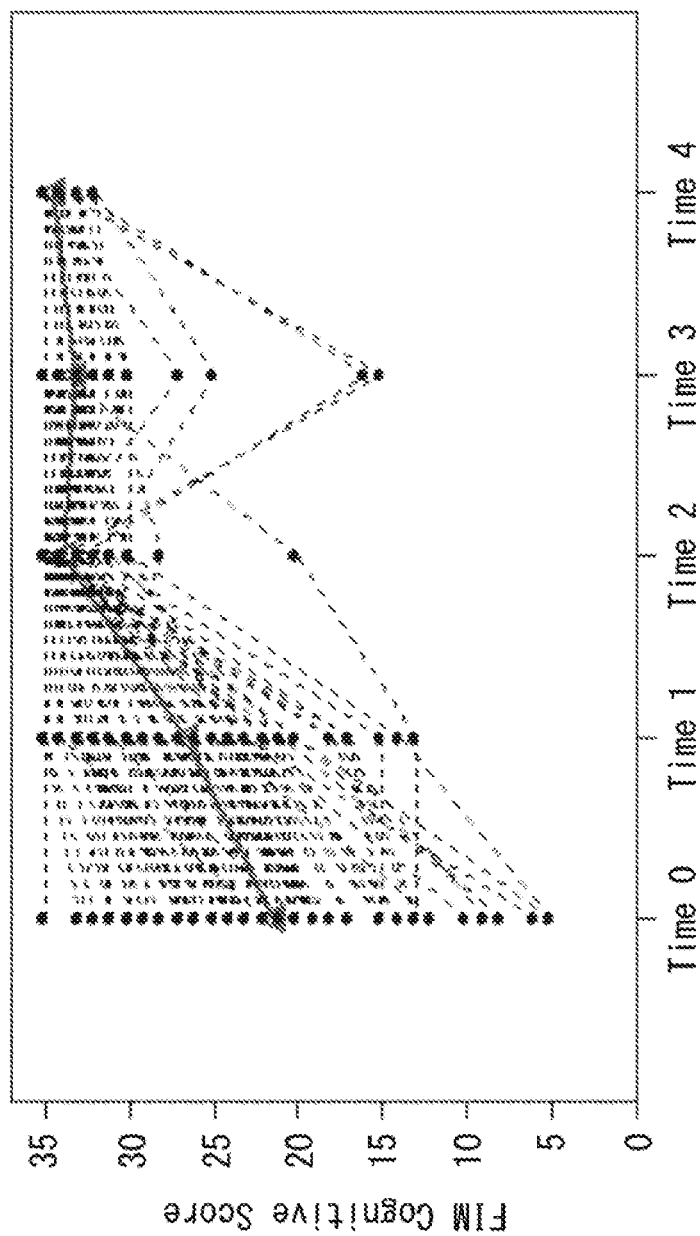
FIG. 10F is a demo of separation of heterogeneous groups as a graph of FIM cognitive score versus time in accordance with an example embodiment.

FIG. 10F is a demo of separation of heterogeneous groups as a graph of FIM cognitive score versus time in accordance with an example embodiment. The Y-axis is FIM cognitive score (ranging from 0 to 35+), and the X-axis is time. The data includes mean value of one of the heterogeneous groups and observed individual value of FIM cognitive score.

Figure 10G:
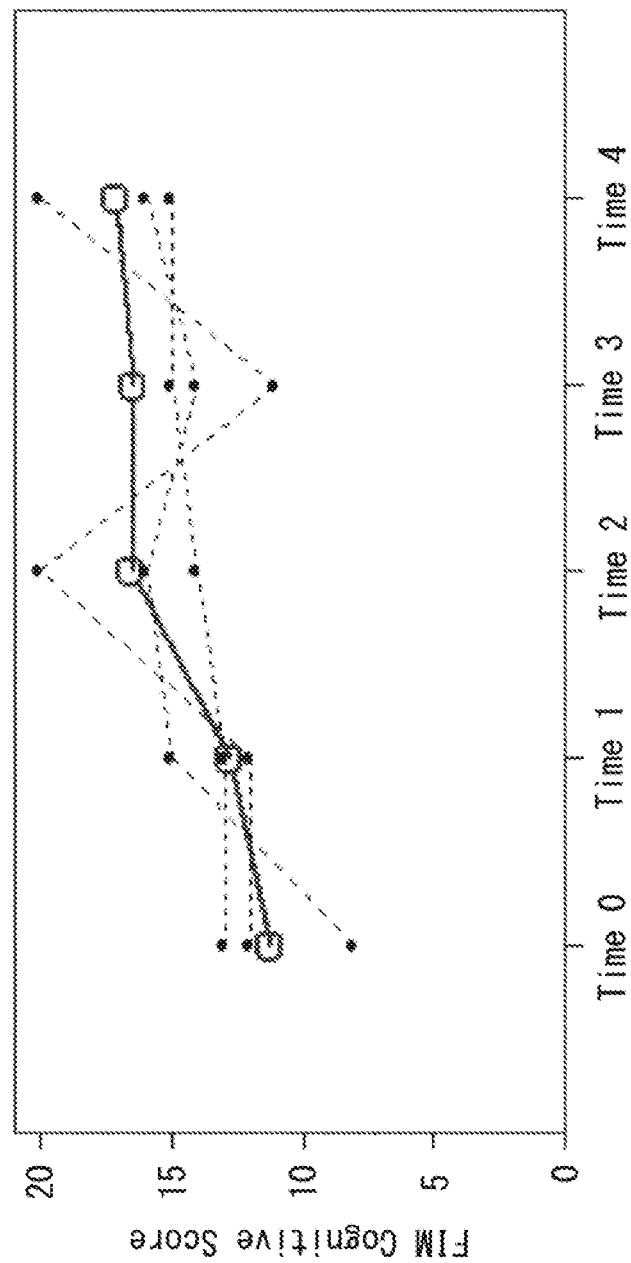
FIG. 10G is a demo of separation of heterogeneous groups as a graph of FIM cognitive score versus time in accordance with an example embodiment.

FIG. 10G is a demo of separation of heterogeneous groups as a graph of FIM cognitive score versus time in accordance with an example embodiment. The Y-axis is FIM cognitive score (ranging from 0 to 30+), and the X-axis is time. The data includes mean value of one of the heterogeneous groups and observed individual value of FIM cognitive score.

Figure 10H:
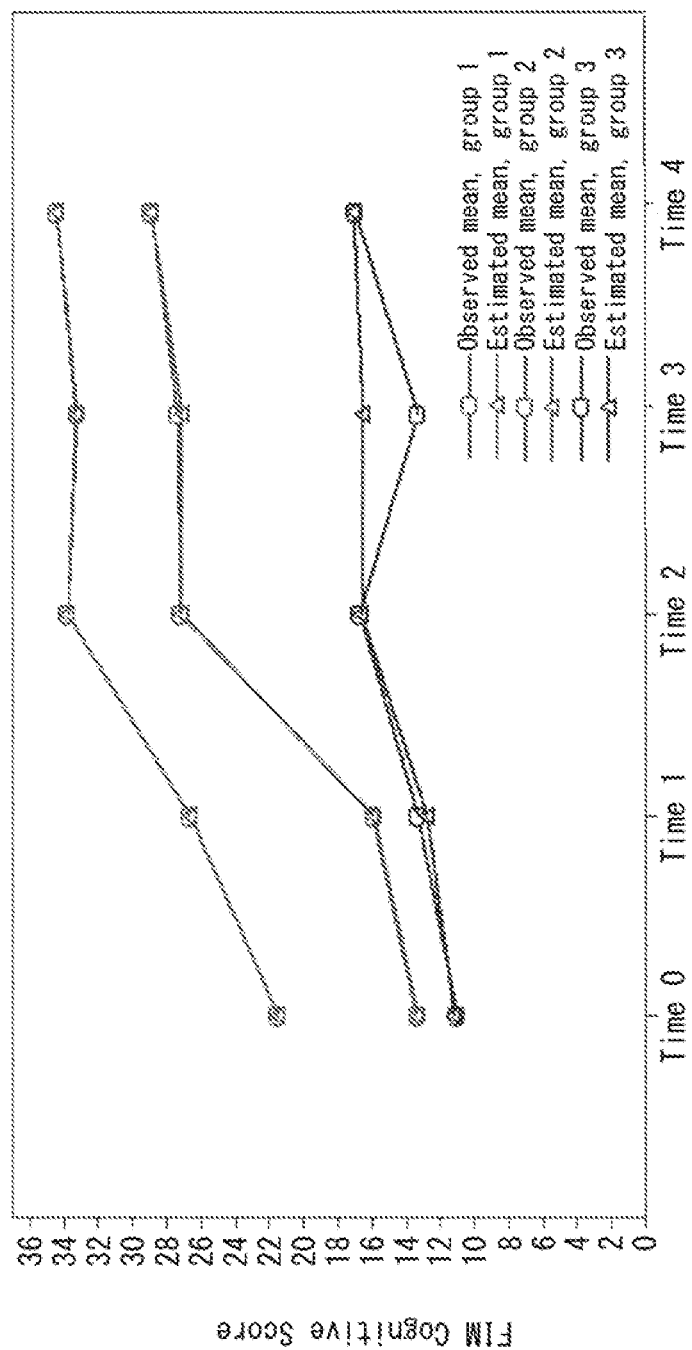
FIG. 10H is a demo of separation of heterogeneous groups as a graph of FIM cognitive score versus time in accordance with an example embodiment.

FIG. 10H is a demo of separation of heterogeneous groups as a graph of FIM cognitive score versus time in accordance with an example embodiment. The Y-axis is FIM cognitive score (ranging from 0 to 20+), and the X-axis is time. The data includes mean value of one of the heterogeneous groups and observed individual value of FIM cognitive score.

Figure 11:
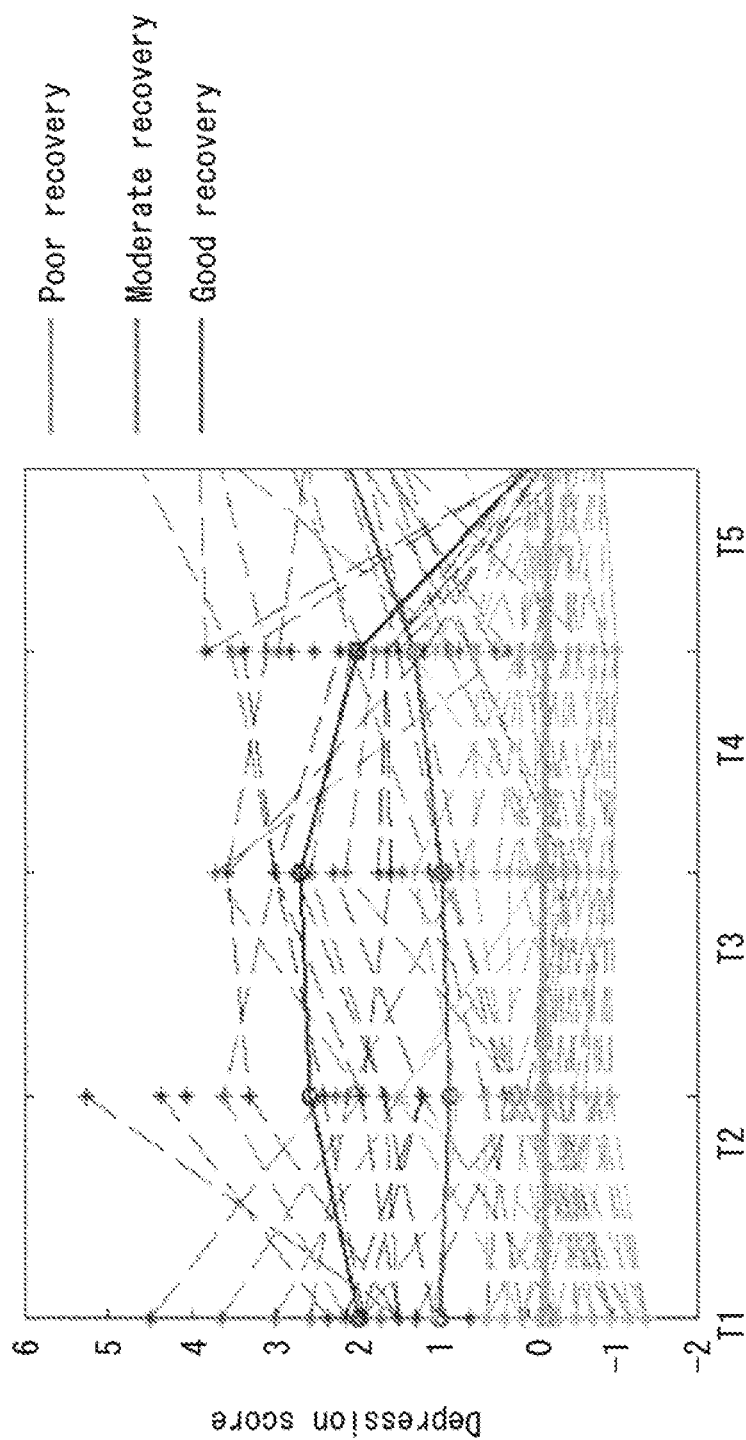
FIG. 11 is a graph showing depression score versus time of three heterogeneous groups of with poor, moderate, and good recoveries in accordance with an example embodiment.

FIG. 11 is a graph showing a depression score versus time of three heterogeneous groups of with poor, moderate, and good recoveries in accordance with an example embodiment. The graph shows three different patient recoveries as poor recovery, moderate recovery, and good recovery. The Y-axis includes depression scores (ranging from −2 to 6), and the X-axis is time.

Figure 12:
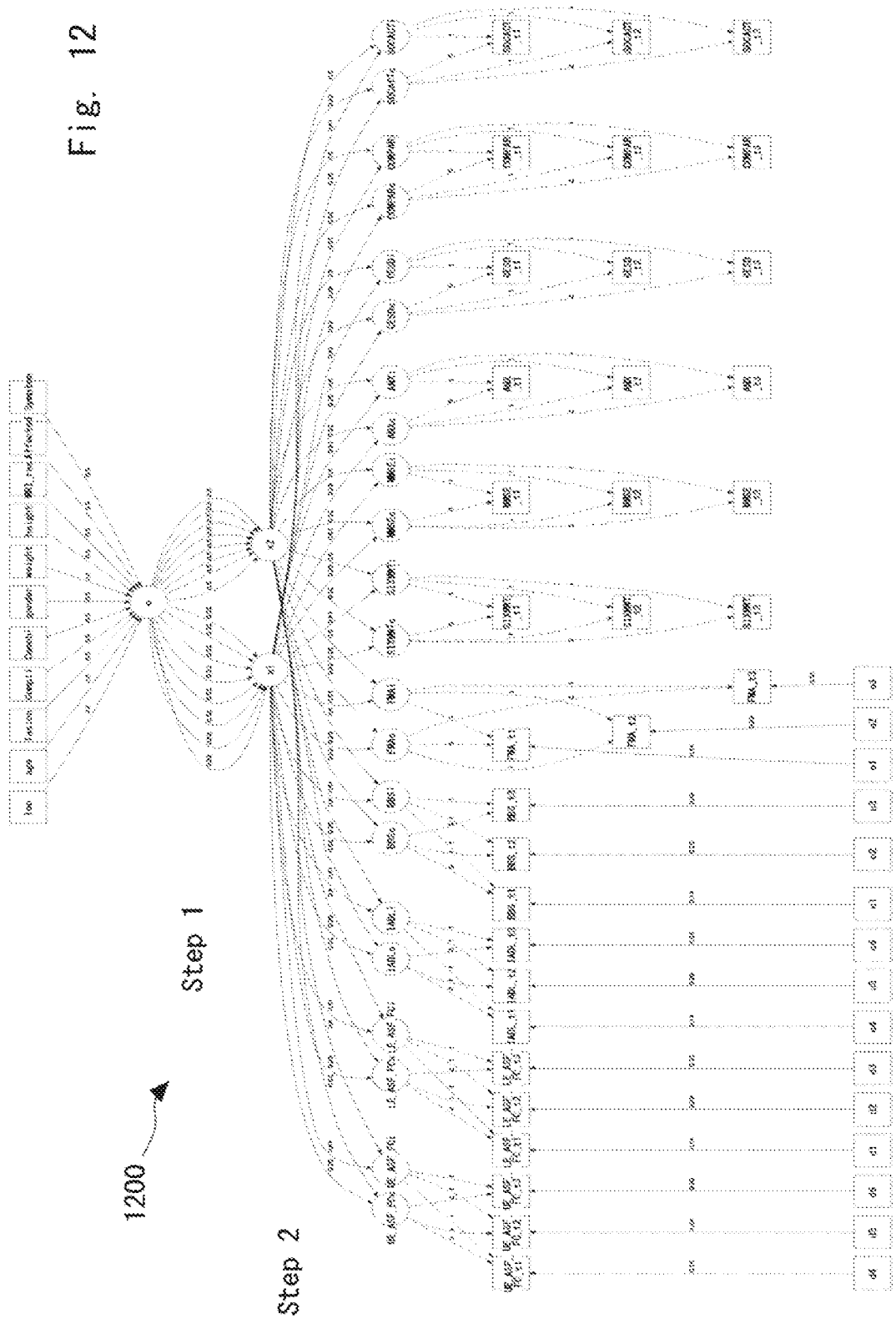
FIG. 12 is a model showing a few variables for longitudinal heterogeneous trajectory analysis and separate heterogeneous groups in accordance with an example embodiment.

FIG. 12 is a model 1200 showing a few variables for longitudinal heterogeneous trajectory analysis and separate heterogeneous groups in accordance with an example embodiment. The variables are provided for process/steps 1 and 2 discussed herein.

Figure 13:
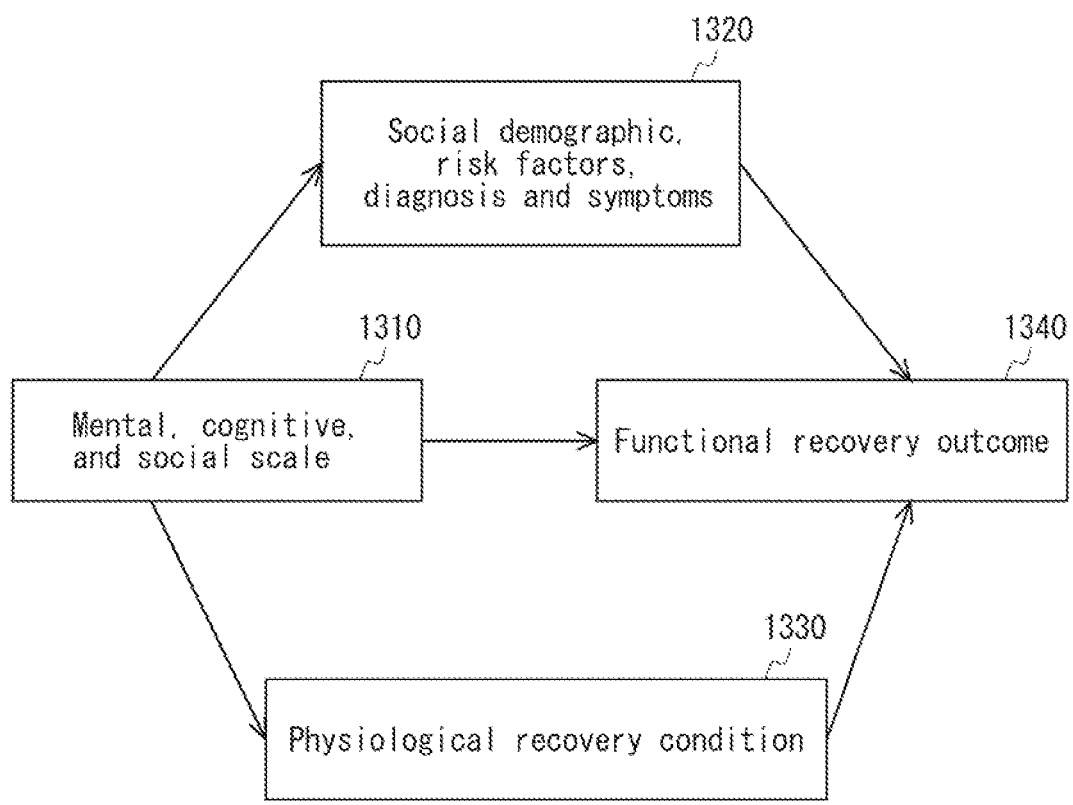
FIG. 13 is a flow diagram of prediction of functional recovery by finding the relations of mental, cognitive and social behaviors, physiological recovery, disease risk and symptoms and functional recovery potential in accordance with an example embodiment.

FIG. 13 is a flow diagram of prediction of functional recovery by finding the relations of mental, cognitive and social behaviors, physiological recovery, disease risk and symptoms and functional recovery potential in accordance with an example embodiment.

Block 1310 includes mental, cognitive, and social scale and couples to or communicates with blocks 1320, 1330, and 1340.

Block 1320 couples to or communicates with blocks 1310 and 1340 and includes social demographic, risk factors, diagnosis and symptoms.

Block 1330 couples to or communicates with blocks 1310 and 1340 and includes physiological recovery condition.

Block 1340 couples to or communicates with blocks 1310, 1320, and 1330 and includes functional recovery outcome.

Figure 14:
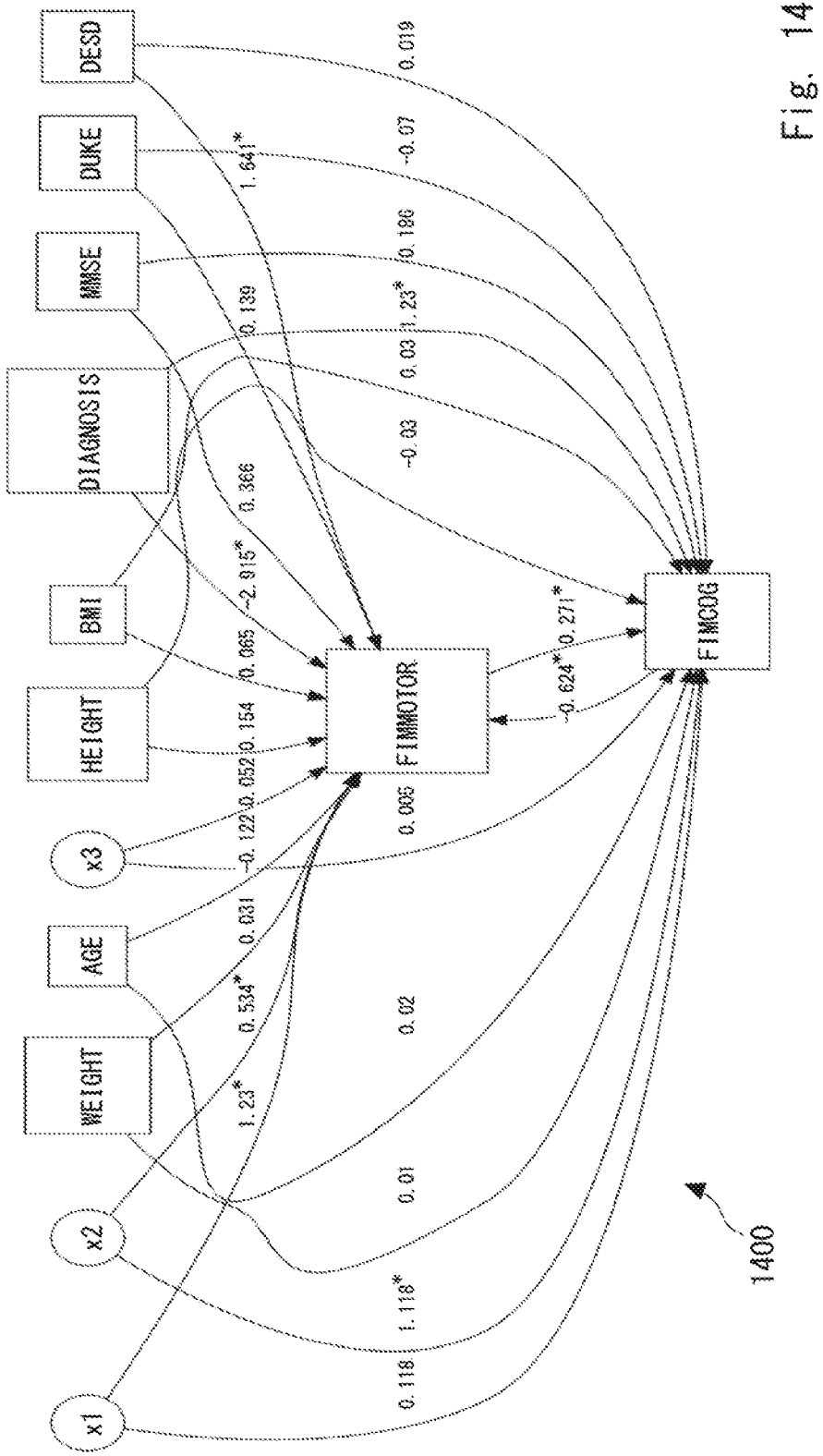
FIG. 14 is a demo of prediction of functional recovery in accordance with an example embodiment.

FIG. 14 a demo 1400 of prediction of functional recovery in accordance with an example embodiment. The model includes patient input information (including weight, age, height, BMI, diagnosis, MMSE, DUKE, and DESD) that couples to or communicates with a FIM Motor that couples to or communicates with FIM COG.

FIG. 15 is a model 1500 showing a few variables for longitudinal heterogeneous trajectory analysis (step 1), separate heterogeneous groups (step 2), and prediction of functional recovery (step 3) in accordance with an example embodiment. The variables are provided for process/steps 1-3 discussed herein.

As used herein, "good recovery potential" is a group of patients in which their functional recoveries are progressing quickly and may have a full functional ability within 6 months.

As used herein, "moderate recovery potential" is a group of patients in which their functional recoveries are progressing slowly and may have a moderate functional ability within 6 months.

As used herein, "poor recovery potential" is a group of patients in which their functional recoveries are not much progressing and may have a limited functional ability within 6 months.

As used herein, "heterogeneous trajectories" are the trajectories of individual assessment outcome over a longitudinal time point which have one or more pattern of trajectories such as some trajectories are random intercept and random slope in their pattern, some trajectories are constant intercept and random slope in their pattern. Therefore, their trajectories patterns are not homogeneous among individuals and may have one or more different patterns and so called heterogeneous trajectories.

As used herein, "longitudinal study" is an investigation in which outcomes and possible treatments or exposures of a patient are collected at multiple follow-up times.

As used herein, "multimodal data" is the data that comes from multiple and independent data sources which tell us different aspect of reality that can be combined afterwards to get more accurate knowledge of it. Examples include but not limited to: integration of data from MRI imaging (image format), MRI imaging report (text format), physiological data (time series data format), and so on.

In some example embodiments, the methods illustrated herein and data and instructions associated therewith, are stored in respective storage devices that are implemented as computer-readable and/or machine-readable storage media, physical or tangible media, and/or non-transitory storage media. These storage media include different forms of memory including semiconductor memory devices such as DRAM, or SRAM, Erasable and Programmable Read-Only Memories (EPROMs), Electrically Erasable and Programmable Read-Only Memories (EEPROMs) and flash memories; magnetic disks such as fixed and removable disks; other magnetic media including tape; optical media such as Compact Disks (CDs) or Digital Versatile Disks (DVDs). Note that the instructions of the software discussed above can be provided on computer-readable or machine-readable storage medium, or alternatively, can be provided on multiple computer-readable or machine-readable storage media distributed in a large system having possibly plural nodes. Such computer-readable or machine-readable medium or media is (are) considered to be part of an article (or article of manufacture). An article or article of manufacture can refer to a manufactured single component or multiple components.

Blocks and/or methods discussed herein can be executed and/or made by a software application, an electronic device, a computer, firmware, hardware, a process, a computer system, and/or an engine (which is hardware and/or software programmed and/or configured to execute one or more example embodiments or portions of an example embodiment). Furthermore, blocks and/or methods discussed herein can be executed automatically with or without instruction from a user.

While exemplary embodiments have been presented in the foregoing detailed description of the present embodiments, it should be appreciated that a vast number of variations exist. It should further be appreciated that the exemplary embodiments are only examples, and are not intended to limit the scope, applicability, operation, or configuration of the invention in any way. Rather, the foregoing detailed description will provide those skilled in the art with a convenient road map for implementing exemplary embodiments of the invention, it being understood that various changes may be made in the function and arrangement of steps and method of operation described in the exemplary embodiments without departing from the scope of the invention as set forth in the appended claims.

For example, the whole or part of the exemplary embodiments disclosed above can be described as, but not limited to, the following supplementary notes.

(Supplementary Note 1)

A computer system, comprising:
 a database that stores multimodal data of a person recovering from a brain injury; and
 a computer that analyzes the multimodal data over multiple intervals that span more than two months of time and includes:
  executing longitudinal heterogeneous trajectory analysis on the multimodal data;
  executing separation of heterogeneous groups that include good recovery potential of the brain injury, moderate recovery potential of the brain injury, and poor recovery potential of the brain injury; and
  predicting, based on the longitudinal heterogeneous trajectory analysis and the separation of the heterogeneous groups, functional recovery of the person from the brain injury.

(Supplementary Note 2)

The computer system of claim 1, wherein the executing longitudinal heterogeneous trajectory analysis on the multimodal data further includes:
 selecting longitudinal time point data;
 fitting a model to the longitudinal time point data using one or more of linear modelling, quadratic modelling, and nonlinear modelling; and
 executing Bayesian information criterion (BIC) to choose a best fit model.

(Supplementary Note 3)

The computer system of claim 1, wherein the separation of heterogeneous groups on the multimodal data further includes:
 selecting longitudinal time point data;
 fitting a model to the longitudinal time point data using one or more of linear modelling, quadratic modelling, and nonlinear modelling;
 clustering latent growth parameters; and
 selecting the person as one of the good recovery potential, the moderate recovery potential, and the poor recovery potential.

(Supplementary Note 4)

The computer system of claim 1, wherein the computer further analyzes the multimodal data and displays a graph of Functional Independence Measure (FIM) cognitive score on a Y-axis versus time on an X-axis for the person.

(Supplementary Note 5)

The computer system of claim 1, wherein the computer further analyzes the multimodal data and generates a model that predicts the functional recovery of the person and includes latent variables of intercept and slope that capture trends of the functional recovery.

(Supplementary Note 6)

The computer system of claim 1, wherein the computer further analyzes the multimodal data of persons recovering from the brain injury and clusters groups of the persons based on cognitive data of the persons, mental data of the persons, social data of the persons, and physiological trajectories that generate latent growth parameters based on individual trend.

(Supplementary Note 7)

The computer system of claim 1, wherein the computer analyzes the multimodal data over multiple intervals that include 72 hours after the brain injury of the person, one month after the brain injury of the person, three months after the brain injury of the person, six months after the brain injury of the person, and one year after the brain injury of the person.

(Supplementary Note 8)

The computer system of claim 1, wherein the multimodal data includes Fugl Meyer Assessment of Motor Recovery of the person, Berg Balance Scale (BBS) of the person, and a walking test of the person.

(Supplementary Note 9)

The computer system of claim 1, wherein the multimodal data includes Mini-Mental State Examination (MMSE) of the person, physiological assessment of the person using EMG and motion sensors, and Functional Independence Measure (FIM) of the person.

(Supplementary Note 10)

The computer system of claim 1, wherein the multimodal data includes a physiological record of the person, a magnetic resonance imaging (MRI) of the brain of the person, rehabilitation records of the person, and demographic data of the person.

(Supplementary Note 11)

The computer system of claim 10, wherein the rehabilitation records include longitudinal assessments by a therapist of a physical condition of the person, a mental condition of the person, and neurological states of the person.

(Supplementary Note 12)

The computer system of claim 1, wherein the functional recovery includes both short-term functional recovery for the person from the brain injury and long-term functional recovery for the person from the brain injury.

(Supplementary Note 13)

A method executed by a computer system, comprising:
storing, in a database, multimodal data of people recovering from a brain injury; and
executing, with a processor, instructions stored in memory that provide analysis of the multimodal data over multiple intervals that span more than two months of time and include:
executing longitudinal heterogeneous trajectory analysis on the multimodal data;
executing separation of heterogeneous groups of the people that include good recovery potential for recovery of the brain injury, moderate recovery potential of the brain injury, and poor recovery potential of the brain injury; and
predicting, based on the longitudinal heterogeneous trajectory analysis and the separation of the heterogeneous groups, functional recovery of a person in the group from the brain injury.

(Supplementary Note 14)

The method of claim 13 wherein executing the longitudinal heterogeneous trajectory analysis on the multimodal data further comprises:
selecting longitudinal time point data;
fitting a model to the longitudinal time point data using one or more of linear modelling, quadratic modelling, and nonlinear modelling; and
executing Bayesian information criterion (BIC) to choose a best fit model.

(Supplementary Note 15)

The method of claim 13 wherein the separation of heterogeneous groups on the multimodal data further comprises:
selecting longitudinal time point data;
fitting a model to the longitudinal time point data using one or more of linear modelling, quadratic modelling, and nonlinear modelling;
clustering latent growth parameters; and
selecting the person as one of the good recovery potential, the moderate recovery potential, and the poor recovery potential.

(Supplementary Note 16)

The method of claim 13 further comprising:
displaying a graph of Functional Independence Measure (FIM) cognitive score on a Y-axis versus time on an X-axis for the person.

(Supplementary Note 17)

The method of claim 13 further comprising:
clustering groups of the people based on cognitive data of the people, mental data of the people, social data of the people, and physiological trajectories that generate latent growth parameters based on individual trend.

(Supplementary Note 18)

The method of claim 13 further comprising:
analyzing the multimodal data over the multiple intervals that include a one month time interval from a date of the brain injury of the person, a three month time interval from the date of the brain injury of the person, and a six month time interval from the date of the brain injury of the person.

(Supplementary Note 19)

The method of claim 13, wherein the multimodal data includes Fugl Meyer Assessment of Motor Recovery of the person, Berg Balance Scale (BBS) of the person, a walking test of the person, a Mini-Mental State Examination (MMSE) of the person, a Functional Independence Measure (FIM) of the person, and a magnetic resonance imaging (MRI) of the brain of the person.

This application is based upon and claims the benefit of priority from Singapore Patent Application No. 10201807529V, filed on Sep. 3, 2018, the disclosure of which is incorporated herein in its entirety by reference.

REFERENCE SIGNS LIST

110 Patient Record
120 Patient Record Database
130 Current Patient Data
140 Sensors
150 Computer
152 Processing Unit
153 Memory
154 Display
155 Domain Knowledge Engine
156 Prediction Engine
158 Report Result Generator
200 Patient's physiological record
210 Domain Knowledge Engine
220 Baseline clinical and longitudinal rehabilitation and physiological record database
230 Patient's clinical record
240 Patient's rehabilitation record

What is claimed is:

1. A computer system, comprising:
a database that stores multimodal data of a person recovering from a brain injury;
a memory storing instructions; and
a processor configured to execute the instructions to implement analyzing the multimodal data over multiple intervals that span more than two months of time by:
executing longitudinal heterogeneous trajectory analysis on the multimodal data;
executing separation of heterogeneous groups that include good recovery potential of the brain injury, moderate recovery potential of the brain injury, and poor recovery potential of the brain injury;
predicting, based on the longitudinal heterogeneous trajectory analysis and the separation of the heterogeneous groups, functional recovery of the person from the brain injury; and
outputting a display of a graph comprising plots representing the predicted functional recovery of the person over a sequence of time.

2. The computer system of claim 1, wherein the executing longitudinal heterogeneous trajectory analysis on the multimodal data further includes:
selecting longitudinal time point data;
fitting a model to the longitudinal time point data using one or more of linear modelling, quadratic modelling, and nonlinear modelling; and executing Bayesian information criterion (BIC) to choose a best fit model.

3. The computer system of claim 1, wherein the separation of heterogeneous groups on the multimodal data further includes:
   selecting longitudinal time point data;
   fitting a model to the longitudinal time point data using one or more of linear modelling, quadratic modelling, and nonlinear modelling;
   clustering latent growth parameters; and
   selecting the person as one of the good recovery potential, the moderate recovery potential, and the poor recovery potential.

4. The computer system of claim 1, wherein the processor is further configured to execute the instructions to implement analyzing the multimodal data by displaying the graph as a Functional Independence Measure (FIM) cognitive score on a Y-axis versus time on an X-axis for the person.

5. The computer system of claim 1, wherein the processor is further configured to execute the instructions to implement analyzing the multimodal data by generating a model that predicts the functional recovery of the person and includes latent variables of intercept and slope that capture trends of the functional recovery.

6. The computer system of claim 1, wherein the processor is further configured to execute the instructions to implement analyzing the multimodal data by analyzing multimodal data of persons recovering from the brain injury and clustering groups of the persons based on cognitive data of the persons, mental data of the persons, social data of the persons, and physiological trajectories that generate latent growth parameters based on individual trend.

7. The computer system of claim 1, wherein the processor is further configured to execute the instructions to implement analyzing the multimodal data by analyzing the multimodal data over multiple intervals that include 72 hours after the brain injury of the person, one month after the brain injury of the person, three months after the brain injury of the person, six months after the brain injury of the person, and one year after the brain injury of the person.

8. The computer system of claim 1, wherein the multimodal data includes Fugl Meyer Assessment of Motor Recovery of the person, Berg Balance Scale (BBS) of the person, and a walking test of the person.

9. The computer system of claim 1, wherein the multimodal data includes Mini-Mental State Examination (MMSE) of the person, physiological assessment of the person using EMG and motion sensors, and Functional Independence Measure (FIM) of the person.

10. The computer system of claim 1, wherein the multimodal data includes a physiological record of the person, a magnetic resonance imaging (MRI) of the brain of the person, rehabilitation records of the person, and demographic data of the person.

11. The computer system of claim 10, wherein the rehabilitation records include longitudinal assessments by a therapist of a physical condition of the person, a mental condition of the person, and neurological states of the person.

12. The computer system of claim 1, wherein the functional recovery includes both short-term functional recovery for the person from the brain injury and long-term functional recovery for the person from the brain injury.

13. A method executed by a computer system comprising at least one hardware processor, the method comprising:
   storing, in a database, multimodal data of people recovering from a brain injury; and
   executing, by the at least one hardware processor, instructions stored in memory that provide analysis of the multimodal data over multiple intervals that span more than two months of time and include:
   executing, by the at least one hardware processor, longitudinal heterogeneous trajectory analysis on the multimodal data;
   executing, by the at least one hardware processor, separation of heterogeneous groups of the people that include good recovery potential for recovery of the brain injury, moderate recovery potential of the brain injury, and poor recovery potential of the brain injury;
   predicting, by the at least one hardware processor and based on the longitudinal heterogeneous trajectory analysis and the separation of the heterogeneous groups, functional recovery of a person in the group from the brain injury; and
   outputting a display of a graph comprising plots representing the predicted functional recovery of the person over a sequence of time.

14. The method of claim 13 wherein executing the longitudinal heterogeneous trajectory analysis on the multimodal data further comprises:
   selecting longitudinal time point data;
   fitting a model to the longitudinal time point data using one or more of linear modelling, quadratic modelling, and nonlinear modelling; and
   executing Bayesian information criterion (BIC) to choose a best fit model.

15. The method of claim 13 wherein the separation of heterogeneous groups on the multimodal data further comprises:
   selecting longitudinal time point data;
   fitting a model to the longitudinal time point data using one or more of linear modelling, quadratic modelling, and nonlinear modelling;
   clustering latent growth parameters; and
   selecting the person as one of the good recovery potential, the moderate recovery potential, and the poor recovery potential.

16. The method of claim 13 further comprising:
   displaying the graph as a Functional Independence Measure (FIM) cognitive score on a Y-axis versus time on an X-axis for the person.

17. The method of claim 13 further comprising:
   clustering groups of the people based on cognitive data of the people, mental data of the people, social data of the people, and physiological trajectories that generate latent growth parameters based on individual trend.

18. The method of claim 13 further comprising:
   analyzing the multimodal data over the multiple intervals that include a one month time interval from a date of the brain injury of the person, a three month time interval from the date of the brain injury of the person, and a six month time interval from the date of the brain injury of the person.

19. The method of claim 13, wherein the multimodal data includes Fugl Meyer Assessment of Motor Recovery of the person, Berg Balance Scale (BBS) of the person, a walking test of the person, a Mini-Mental State Examination (MMSE) of the person, a Functional Independence Measure (FIM) of the person, and a magnetic resonance imaging (MRI) of the brain of the person.

20. A non-transitory computer readable medium having stored thereon instructions which, when executed by a computer comprising at least one hardware processor, make the computer carry out a method comprising:

storing, in a database, multimodal data of people recovering from a brain injury;

executing, by the at least one hardware processor, the instructions that provide analysis of the multimodal data over multiple intervals that span more than two months of time;

executing, by the at least one hardware processor, longitudinal heterogeneous trajectory analysis on the multimodal data;

executing, by the at least one hardware processor, separation of heterogeneous groups of the people that include good recovery potential for recovery of the brain injury, moderate recovery potential of the brain injury, and poor recovery potential of the brain injury; and predicting, by the at least one hardware processor and based on the longitudinal heterogeneous trajectory analysis and the separation of the heterogeneous groups, functional recovery of a person in the group from the brain injury.

* * * * *